United States Patent
Chen et al.

(10) Patent No.: US 6,458,383 B2
(45) Date of Patent: Oct. 1, 2002

(54) PHARMACEUTICAL DOSAGE FORM FOR ORAL ADMINISTRATION OF HYDROPHILIC DRUGS, PARTICULARLY LOW MOLECULAR WEIGHT HEPARIN

(75) Inventors: Feng-Jing Chen, Salt Lake City, UT (US); Mahesh V. Patel, Salt Lake City, UT (US); David T. Fikstad, Salt Lake City, UT (US)

(73) Assignee: Lipocine, Inc., Salt Lake City, UT (US)

(*) Notice: Subject to any disclaimer, the term of this patent is extended or adjusted under 35 U.S.C. 154(b) by 0 days.

(21) Appl. No.: 09/751,968

(22) Filed: Dec. 29, 2000

Related U.S. Application Data

(63) Continuation-in-part of application No. 09/375,636, filed on Aug. 17, 1999, now Pat. No. 6,309,663.

(30) Foreign Application Priority Data

Jul. 10, 2000 (WO) ............................... PCT/US00/18807

(51) Int. Cl.$^7$ ................................................. A61K 9/48
(52) U.S. Cl. ........................ 424/451; 424/450; 424/451; 424/455; 424/456; 424/463; 424/489; 424/499; 424/502; 424/435; 424/464; 424/434; 514/937; 514/938; 514/939; 514/940; 514/941; 514/942; 514/943; 514/975; 514/56
(58) Field of Search ................................. 424/450, 451, 424/455, 456, 463, 489, 499, 502, 435, 464; 514/937–943, 975, 56

(56) References Cited

U.S. PATENT DOCUMENTS

| | | |
|---|---|---|
| 3,510,561 A | 5/1970 | Koh et al. |
| 4,156,719 A | 5/1979 | Sezaki et al. |
| 4,239,754 A | 12/1980 | Sache et al. |
| 4,388,307 A | 6/1983 | Cavanak |
| 4,572,915 A | 2/1986 | Crooks |
| 4,579,730 A | 4/1986 | Kidron et al. |
| 4,654,327 A | 3/1987 | Teng |
| 4,656,161 A | 4/1987 | Herr |
| 4,695,450 A | 9/1987 | Bauer |
| 4,703,042 A | 10/1987 | Bodor |
| 4,713,246 A | 12/1987 | Begurn et al. |
| 4,719,239 A | 1/1988 | Muller et al. |
| 4,727,109 A | 2/1988 | Schmidt et al. |
| 4,944,949 A | 7/1990 | Story et al. |
| 4,994,439 A | 2/1991 | Longnecker et al. |

(List continued on next page.)

FOREIGN PATENT DOCUMENTS

| | | |
|---|---|---|
| EP | 0036145 | 9/1981 |
| WO | WO 84/02076 | 6/1984 |
| WO | WO 88/00059 | 1/1988 |
| WO | WO 93/06921 | 4/1993 |
| WO | WO 95/34287 | 12/1995 |
| WO | WO 96/17597 | 6/1996 |

OTHER PUBLICATIONS

Alvarez et al. (1989), "The Role of Calcium Ions and Bile Salts on the Pancreatic Lipase–Catalyzed Hydrolysis of Triglycefide Emulsions Stabilized with Lecithin," *Pharmaceutical Research* 6(6):449–457.

Baluom et al. (1998), "The Importance of Intestinal Residence Time of Absorption Enhancer on Drug Absorption and Implication on Formulative Considerations," *International Journal of Pharmaceutics* 176:21–30.

Bates et al. (1975), "Bioavailability of Micronized Griseofulvin from Corn Oil–in–Water Emulsion, Aqueous Suspension, and Commercial Tablet Dosage Forms in Humans," *Journal of Pharmaceutical Sciences* 64(5):793–797.

Bernkop–Schnürch (1998), "The Use of Inhibitory Agents to Overcome the Enzymatic Barrier to Perorally Administered Therapeutic Peptides and Proteins," *Journal of Controlled Release* 52:1–16.

Charman et al. (1997), "Physiochemical and Physiological Mechanisms for the Effects of Food on Drug Absorption: The Role of Lipids and pH," *Journal of Pharmaceutical Sciences* 86(3):269–282.

Gennaro (1985), *Remington's Pharmaceutical Sciences*, Chapter 20, pp. 293–300.

Hörter et al. (1997), "Influence of Physicochemical Properties on Dissolution of Drugs in the Gastrointestinal Tract," *Advanced Drug Delivery Reviews* 25:3–14.

Johnson (1997), "Gastrointestinal Physiology," C V Morby Co., St. Louis, Houston, Texas, pp. 25–26, 93, 106, 133–134, and 136–137.

LeCluyse et al. (1997), "In Vitro Models for Selection of Development Candidates. Permeability Studies to Define Mechanisms of Absorption Enhancement," *Advanced Drug Delivery Reviews* 23:163–183.

MacGregor et al. (1997), "Influence of Lipolysis on Drug Absorption From the Gastro–Intestinal Tract," *Advanced Drug Delivery Reviews* 25:33–46.

(List continued on next page.)

*Primary Examiner*—Thurman K. Page
*Assistant Examiner*—Lakshmi Channavajjala
(74) *Attorney, Agent, or Firm*—Reed & Associates; Dianne E. Reed

(57) ABSTRACT

A delayed release pharmaceutical dosage form for oral administration of a hydrophilic drug, e.g., a polysaccharide drug such as low molecular weight heparin, are provided. The dosage form comprises a composition of: (a) a therapeutically effective amount of low molecular weight heparin; (b) a bile salt or bile acid; (c) at least one surfactant selected from hydrophilic surfactants, lipophilic surfactants, and mixtures thereof; and a means for delaying release of the composition from the dosage form following oral administration. Osmotic drug delivery systems for oral administration of a hydrophilic drug are also provided, wherein an osmotically activated device houses the drug, a bile salt or bile acid, and at least one surfactant selected from the group consisting of hydrophilic surfactants, lipophilic surfactants, and mixtures thereof. Methods for administering hydrophilic drugs, particularly polysaccharide drugs such as low molecular weight heparin, are also provided.

94 Claims, No Drawings

U.S. PATENT DOCUMENTS

| | | |
|---|---|---|
| 5,071,643 A | 12/1991 | Yu et al. |
| 5,120,710 A | 6/1992 | Liedtke |
| 5,145,684 A | 9/1992 | Liversidge et al. |
| 5,206,219 A | 4/1993 | Desai |
| 5,244,925 A | 9/1993 | Wretlind et al. |
| 5,252,339 A * | 10/1993 | Cristofori et al. ............ 424/479 |
| 5,342,625 A | 8/1994 | Hauer et al. |
| 5,350,741 A | 9/1994 | Takada |
| 5,364,632 A | 11/1994 | Benita et al. |
| 5,384,133 A * | 1/1995 | Boyes et al. ................. 424/501 |
| 5,444,041 A | 8/1995 | Owen et al. |
| 5,500,224 A | 3/1996 | Vranckx et al. |
| 5,532,002 A | 7/1996 | Story |
| 5,589,455 A | 12/1996 | Woo |
| 5,614,491 A | 3/1997 | Walch et al. |
| 5,616,330 A | 4/1997 | Kaufman et al. |
| 5,622,721 A | 4/1997 | Dansereau et al. |
| 5,626,869 A | 5/1997 | Nyqvist et al. |
| 5,633,226 A | 5/1997 | Owen et al. |
| 5,639,474 A | 6/1997 | Woo |
| 5,639,724 A | 6/1997 | Cavanak |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslöf et al. |
| 5,681,584 A * | 10/1997 | Savastano et al. .......... 424/473 |
| 5,686,105 A | 11/1997 | Kelm et al. |
| 5,688,761 A | 11/1997 | Owen et al. |
| 5,707,648 A * | 1/1998 | Yiv ............................ 424/450 |
| 5,714,477 A | 2/1998 | Einarsson |
| 5,731,355 A | 3/1998 | Jones et al. |
| 5,736,161 A | 4/1998 | Garces et al. |
| 5,741,822 A | 4/1998 | Yesair |
| 5,747,066 A | 5/1998 | Pittrof et al. |
| 5,766,629 A | 6/1998 | Cho et al. |
| 5,853,748 A | 12/1998 | New |
| 5,858,398 A | 1/1999 | Cho |
| 5,858,401 A | 1/1999 | Bhalani et al. |

OTHER PUBLICATIONS

Pouton (1997), "Formulation of Self–Emulsifying Drug Delivery Systems," *Advanced Drug Delivery Reviews* 25:47–58.

Reymond et al., "In Vitro Model for Ciclosporin Intestinal Absorption in Lipid Vehicles," Pharmaceutical Research 5(10):673–676.

Tarr et al. (1989), "Enhanced Intestinal Absorption of Cyclosporine in Rats Through The Reduction of Emulsion Droplet Size," *Pharmaceutical Research* 6(1):40–43 (1989).

Wilson et al. (1997), "The Behaviour of Fats and Oils in the Upper G.I. Tract," *Bulletin Technique Gattefossé* 90:13–18.

Winne (1978), "Dependence of Intestinal Absorption in Vivo on the Unstirred Layer," *Archives of Pharmacology* 304:175–181.

Zhi et al. (1995), "Effects of Dietary Fat on Drug Absorption," Clinical Pharmacology and Therapeutics 58(5):487–491.

U.S. patent application Ser. No. 09/375,636, Patel et al., filed Aug. 17, 1999.

Aungst (2000), "Intestinal Permeation Enhancers," *Journal of Pharmaceutical Sciences* 89(4):429–442.

Muranishi (1977), "Potential Absorption of Heparin from the Small Intestine and the Large Intestine in the Presence of Monoolein Mixed Micelles," *Chem. Pharm. Bull.* 24(5):1159–1161.

Muranishi (1990), "Absorption Enhancers," *Critical Reviews in Therapeutic Drug Carrier Systems* 7(1):1–33.

Schott (1990), "Comments on Hydrophile–Lipophile Balance Systems," *Journal of Pharmaceutical Sciences* 79(1):87–88.

* cited by examiner

PHARMACEUTICAL DOSAGE FORM FOR ORAL ADMINISTRATION OF HYDROPHILIC DRUGS, PARTICULARLY LOW MOLECULAR WEIGHT HEPARIN

CROSS-REFERENCE TO RELATED APPLICATIONS

This application is a continuation-in-part of U.S. patent application Ser. No. 09/375,636, filed Aug. 17, 1999, now U.S. Pat. No. 6,309,663, the disclosure of which is hereby incorporated by reference.

TECHNICAL FIELD

The present invention relates generally to drug delivery, and more specifically relates to novel dosage forms, methods and drug delivery systems for enhancing the absorption and therefore the bioavailability of hydrophilic drugs, particularly polysaccharide drugs such as heparin, including low molecular weight heparin. The invention has utility in the fields of pharmaceutical formulation, pharmacology, and medicine.

BACKGROUND

Hydrophilic therapeutic agents frequently present difficult challenges with respect to both formulation and delivery. While these therapeutic agents can be readily soluble in water and easily dissolvable from a given dosage form in the gastrointestinal environment, the absorption of these drugs, because of their high molecular weight and/or hydrophilicity, is severely hampered by the permeation barrier imposed by the intestinal epithelial cell membrane as well as the junctional structure between the epithelial cells. In addition, chemical degradation in the acidic environment of the stomach, enzymatic inactivation, and binding or interference by mucous and other contents of the gastrointestinal (GI) tract can also contribute to the reduced availability of hydrophilic drugs in the GI tract for absorption. As a result, the administration of these hydrophilic drugs such as polysaccharides, peptides, and proteins frequently calls for invasive approaches such as subcutaneous or intravenous injection, resulting in severe restrictions in clinical use and problems with patient compliance.

Heparin is a polysaccharide drug of particular interest and importance because it is a potent anticoagulant drug widely used in the prevention and treatment of thrombosis. It decreases the rate of coagulation by increasing the rate at which antithrombin (also termed "heparin cofactor" or "antithrombin III") inhibits activated coagulation factors, particularly thrombin, a key enzyme in the coagulation cascade. Heparin is a glycosaminoglycan present in the secretory granules of mast cells, and is characterized as a polymer of alternating D-glucuronic acid and N-acetyl-D-glucosamine residues (Bourin et al. (1993), "Glycosaminoglycans and the Regulation of Blood Coagulation," *Biochem. J.* 289:313–330). Heparinoids—derivatives, analogs, fragments, salts, esters, etc. of heparin or heparin like glycosaminoglycan such as chrondroitin, dermatan sulfate, sulfomucopolysaccharide, mesoglycan, sulodexide, etc.— are also of paramount interest as anticoagulants.

Among all the heparins and heparinoids, low molecular weight heparin is of particular interest from a clinical standpoint. The potential advantages of low molecular weight heparin over unfractionated heparin include are numerous. For example, it has been suggested that low molecular weight heparin may be associated with a reduced risk of bleeding complications, possibly due to its more specific action on clotting factor Xa and relatively low action on factor IIa. In addition, low molecular weight heparin has a longer half-life so dosing frequency can be reduced. Because low molecular weight heparin exhibits reduced binding to platelets, the incidence of thrombocytopenia is substantially reduced. Furthermore, the likelihood of bone loss is reduced because low molecular weight heparin tends to bind less strongly to osteoblasts. See Hirsch et al. (1998), "Heparin and Low-Molecular-Weight Heparin. "*Chest* 114:489S-510S.

However, because low molecular weight heparin is still a fairly large molecule and has prominent negative charges, the epithelial cell membrane in the intestine is practically impermeable to the drug, precluding effective oral delivery. As a result, there are several low molecular weight heparins commercially available for various anti-coagulating indications, but only through an invasive delivery approach, subcutaneous injection. Enoxaprin sodium is currently marketed under the trade name Lovenox® by Rhone-Poulenc Rorer. It is obtained by alkaline degradation of heparin benzyl ester derived from porcine intestinal mucosa. Its average molecular weight is about 4500 daltons, characterized by a distribution of no more than 20% less than 2000 daltons, no more than 15% greater than 8000 daltons, and greater that 68% between 2000 to 8000 daltons. It is formulated as a sterile solution for subcutaneous injection that contains 10 mg enoxaparin sodium per 0.1 ml water for injection in each dosage unit. Ardeparin sodium is currently marketed under the trade name Normiflo® by Wyeth-Ayerst Laboratories. It is a partially depolymerized porcine mucosal heparin that has the same molecular subunits as heparin sodium, USP and is available in concentrations of 5000 and 10000 anti-Factor Xa units/0.5 ml for deep (intra-fat) subcutaneous injection. It has an average molecular weight range of 6000±350 daltons. Dalteparin sodium is currently marketed under the trade name Fragmin® by Pharmacia. It is produced through controlled nitrous acid depolymerization of sodium heparin from porcine intestinal mucosa followed by a chromatographic purification process. Its average molecular weight is about 5000 daltons and about 90% of the material within the range of 2000–9000 daltons. It is available as a single-dose, prefilled syringes containing 32 mg dalteparin sodium in 0.2 ml and a multiple-dose vial containing 64 mg per ml for subcutaneous injection.

Clearly, then, there is a need in the art for a pharmaceutical dosage form for non-invasive (e.g., oral) administration of heparin, heparinoids, and particularly low molecular weight heparin, wherein a therapeutically effective amount of the active agent is provided, the dosage form is chemically and physically stable, and patient compliance is improved relative to prior, injectable formulations.

The following references pertain to one or more aspects of the invention and may provide useful background information:

U.S. Pat. No. 3,510,561 to Koh et al. describes a method for enhancing heparin absorption through mucous membranes by co-administering a sulfone and a fatty alcohol along with the heparin.

U.S. Pat. No. 4,156,719 to Sezaki et al. describes a pharmaceutical formulation for rectal administration of a poorly absorbable drug. The formulation is a micellar solution containing the drug, a $C_6$–$C_8$ fatty acid and/or the mono- or di-glyceride thereof, a bile acid and/or a non-ionic surfactant, and water.

U.S. Pat. No. 4,239,754 to Sache et al. describes liposomal formulations for the oral administration of heparin, intended to provide for a prolonged duration of action. The heparin is retained within or on liposomes, which are preferably formed from phospholipids containing acyl chains deriving from unsaturated fatty acids.

U.S. Pat. No. 4,654,327 to Teng pertains to the oral or other enteral administration of heparin in the form of a complex with a quaternary ammonium ion.

U.S. Pat. No. 4,656,161 to Herr describes a method for increasing the enteral absorbability of heparin or heparinoids by orally administering the drug along with a non-ionic surfactant such as polyoxyethylene-20 cetyl ether, polyoxyethylene-20 stearate, other polyoxyethylene (polyethylene glycol)-based surfactants, polyoxypropylene-1 5 stearyl ether, sucrose palmitate stearate, or octyl-β-D-glucopyranoside.

U.S. Pat. No. 4,695,450 to Bauer describes an anhydrous emulsion of a ydrophilic liquid containing polyethylene glycol, a dihydric alcohol such as propylene glycol, or a trihydric alcohol such as glycerol, and a hydrophobic liquid, particularly an animal oil, a mineral oil, or a synthetic oil.

U.S. Pat. No. 4,703,042 to Bodor describes oral administration of a salt of polyanionic heparinic acid and a polycationic species.

U.S. Pat. No. 4,994,439 to Longenecker et al. describes a method for improving the transmembrane absorbability of macromolecular drugs such as peptides and proteins, by co-administering the drug along with a combination of a bile salt or fusidate or derivative thereof and a non-ionic detergent (surfactant).

U.S. Pat. No. 5,688,761 to Owen et al. focuses primarily on the delivery of peptide drugs using a water-in-oil microemulsion formulation that readily converts to an oil-in-water emulsion by the addition of an aqueous fluid, whereby the peptide or other water-soluble drug is released for absorption by the body. U.S. Pat. Nos. 5,444,041, 5,646,109 and 5,633,226 to Owen et al. are also directed to water-in-oil microemulsions for delivering biologically active agents such as proteins or peptides, wherein the active agent is initially stored in the internal water phase of the emulsion, but is released when the composition converts to an oil-in-water emulsion upon mixing with bodily fluids.

U.S. Pat. No. 5,714,477 to Einarsson describes a method for improving the bioavailability of heparin, heparin fragments or their derivatives by administering the active agent in combination with one or several glycerol esters of fatty acids.

U.S. Pat. No. 5,853,749 to New describes a formulation for buffering the gut to a pH in the range of 7.5 to 9 by coadministering a biologically active agent with a bile acid or salt and a buffering agent.

Muranishi (1990), "Absorption Enhancers," *Critical Reviews in Therapeutic Drug Carrier Systems* 7 (1):1–33, provides an overview of absorption enhancing compounds for macromolecular drugs. Among the numerous enhancing compounds mentioned are medium chain fatty acids ($C_6$–$C_{12}$) such as sodium caprate, and medium chain monoglycerides such as glyceryl-1-monocaprate, dicaprate and tricaprate.

Aungst (2000), "Intestinal Permeation Enhancers," *J Pharm. Sci*. 89(4):429–442, provides an overview of compounds and methods for enhancing intestinal permeation of drugs, and mentions, for example, fatty acids, surfactants and medium-chain glycerides.

SUMMARY OF THE INVENTION

Accordingly, it is a primary object of the invention to address the above-mentioned need in the art by providing a delayed release pharmaceutical dosage form, composition, method and drug delivery system for enhancing the transmembrane absorption of a hydrophilic drug.

It is another object of the invention to provide such a dosage form, composition method and delivery system wherein the hydrophilic drug is heparin.

It is another object of the invention to provide such a dosage form, composition, method and delivery system wherein the hydrophilic drug is low molecular weight heparin.

It is still another object of the invention to provide a composition for administration of a hydrophilic drug, wherein the composition is comprised of a hydrophilic drug, a bile salt or bile acid, and at least one surfactant, and each of the aforementioned components is solubilized or suspended in the composition and/or present as a coating.

It is still another object of the invention to provide such a composition additionally containing a solubilizer.

It is yet another object of the invention to provide such a composition in the form of enterically coated capsules, tablets, caplets, or multiparticulate carriers such as particles, pellets, granules and beads.

It is a further object of the invention to provide a method and delivery system for the administration of a hydrophilic drug, wherein the drug, a bile salt or bile acid, and at least one surfactant are present in a single dosage form.

It is still a further object of the invention to provide a method and delivery system for the administration of a hydrophilic drug, wherein the drug, a bile salt or bile acid, and at least one surfactant are present in different dosage forms.

It is still an additional object of the invention to provide a dosage form comprised of an osmotically activated device in which a semipermeable membrane encapsulates a bile salt or bile acid, at least one surfactant as provided herein, and a hydrophilic drug.

Additional objects, advantages and novel features of the invention will be set forth in part in the description which follows, and in part will become apparent to those skilled in the art upon examination of the following, or may be learned by practice of the invention.

In one embodiment, then, invention is directed to a delayed release pharmaceutical dosage form for oral administration of low molecular weight heparin, wherein the dosage form comprises a composition of: (a) a therapeutically effective amount of low molecular weight heparin; (b) a bile salt or bile acid; (c) at least one surfactant selected from the group consisting of hydrophilic surfactants, lipophilic surfactants, and mixtures thereof, and (d) a means for delaying release of the composition from the dosage form following oral administration. In a preferred embodiment, the composition further includes a solubilizer to ensure good solubilization and/or dissolution of one or more components in the composition.

The dosage form is not limited with respect to size, shape or general configuration, and may comprise, for example, a capsule, a tablet or a caplet, or a plurality of particles, granules, beads, or pellets that may or may not be encapsulated.

Furthermore, either the heparin or the bile salt or bile acid may be present as a coating.

In addition, the dosage form or components of the dosage form may be enterically coated; for example, a capsule or tablet may be enterically coated, and multiparticulate dosage forms such as drug-containing particles, pellets, granules and beads may be enterically coated as well. The enteric coating will generally comprise a bioerodible, gradually hydrolyzable and/or gradually water-soluble material, suitable for providing a desired delayed release profile.

With respect to the bile salt or acid, any bile salt or acid may be employed, so long as the selected compound is at least partially solubilized or suspended in the composition. To ensure good solubilization and/or dissolution of the bile salt or acid, and to minimize precipitation thereof, additional formulation-aiding excipients may be incorporated into the aforementioned dosage form. Such excipients include, for example, bufferants, cosolvents, complexing agents, and crystal growth inhibitors. Additionally, processing techniques such as size reduction, co-precipitation, coacervation, lyophilizing, spray drying, eutectic mixing, solid solutioning or other appropriate techniques may be used to make the bile salt or acid more amenable to rapid dissolution. If suspended, the bile salt or acid can be in any of a number of forms, e.g., crystalline, amorphous, nanosized, micronized, or milled.

Suitable hydrophilic surfactants will generally have an HLB value of at least 10, while suitable lipophilic surfactants will generally have an HLB value of or less than about 10. The co-administration of low molecular weight heparin with a bile salt or acid and at least one surfactant as provided herein substantially enhances the transmembrane absorption of the drug.

While not wishing to be bound by theory, it is proposed that the substantially homogeneous, optically clear aqueous dispersion that results immediately upon contact with an aqueous medium such as gastrointestinal fluid makes the drug immediately available for bioabsorption, i.e., the drug is rapidly and effectively "presented" to a target absorption site within the body. The optically clear aqueous dispersion that is formed is generally characterized as having an absorbance of less than about 0.3 at 400 nm measured at 100x dilution. In another embodiment, a method is provided for administering low molecular weight heparin to a patient, the method comprising administering a therapeutically effective amount of the drug along with a bile salt or acid and at least one surfactant selected from the group consisting of hydrophilic surfactants, lipophilic surfactants, and mixtures thereof. Typical dosages for orally administered low molecular weight heparin using the dosage forms of the invention are on the order of 700 to 400,000 IU/day, generally in the range of about 2500 to 10,000 IU/day, while typical dosages for orally administered unfractionated heparin are on the order of 2,500 to 800,000 Units/day. Generally, the drug will be given for the treatment or prevention of thrombosis.

In still another embodiment, drug delivery systems are provided that comprise an osmotically activated device, i.e., an osmotically activated tablet or capsule, which houses a therapeutically effective amount of a hydrophilic drug, a bile salt or bile acid, and at least one surfactant selected from the group consisting of hydrophilic surfactants, lipophilic surfactants, and mixtures thereof. In this embodiment, the drug-containing composition is encapsulated in a semipermeable membrane or barrier containing a small orifice. As known in the art with respect to so-called "osmotic pump" drug delivery devices, the semipermeable membrane allows passage of water in either direction, but not drug or other components of the drug-containing composition. Therefore, when the device is exposed to aqueous fluids, water will flow into the device due to the osmotic pressure differential between the interior and exterior of the device, and as water flows into the device, the drug-containing formulation in the interior will be "pumped" out through the orifice. The rate of drug release dD/dt, will be equivalent to the inflow rate of water times the drug concentration. In a preferred embodiment, the osmotically activated device is enterically coated with a coating material effective to provide the desired delayed release profile.

In a related embodiment, a drug delivery system is provided for oral administration of a polysaccharide drug, the system comprised of a first dosage form and a second dosage form, wherein the first dosage form contains a therapeutically effective amount of the polysaccharide drug, and the second dosage form contains a bile salt or bile acid in combination with at least one surfactant selected from hydrophilic surfactants, lipophilic surfactants, and mixtures thereof, wherein at least one of the dosage forms is a delayed release dosage form, e.g., coated with an enteric coating. The polysaccharide drug may be, for example, glucosamine, a glycosaminoglycan, dextran, xylan, pentasaccharide, polygalacturonic acid, polymannuronic acid, chitin, pharmaceutically acceptable salts, esters or other derivatives thereof, and combinations of any of the foregoing. The dosage forms may be administered simultaneously or sequentially; in the latter case, either the first dosage form may be administered first, followed by administration of the second dosage form, or the second dosage form may be administered first, followed by administration of the first dosage form.

DETAILED DESCRIPTION OF THE INVENTION

I. Definitions and Overview

Before the present formulations and methods of use are disclosed and described, it is to be understood that unless otherwise indicated this invention is not limited to specific pharmacologically active agents, specific pharmaceutical carriers, or to particular administration regimens, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a polysaccharide drug" includes a single polysaccharide drug or mixtures of such two or more such drugs, reference to "a surfactant" refers to a single surfactant or mixtures of different surfactants, and the like.

In this specification and in the claims that follow, reference will be made to a number of terms, which shall be defined to have the following meanings:

"Optional" or "optionally" means that the subsequently described circumstance ay or may not occur, so that the description includes instances where the circumstance ccurs and instances where it does not.

The terms "active agent," "drug" and "pharmacologically active agent" are used interchangeably herein to refer to a chemical material or compound which, when administered to an organism (human or animal, generally human) induces a desired pharmacologic effect. In the context of the present invention, the terms refer to a hydrophilic drug with aqueous solubility greater than about 100 µg/ml, e.g., polysaccharides and other macromolecules such as peptides, proteins, peptidomimetics, cytokines, nucleotides, nucleosides, genetic materials, toxoids, serum vaccines or combinations thereof. In a preferred embodiment, the hydrophilic drug is a polysaccharide drug capable of being delivered orally.

The term "polysaccharide" is intended to include naturally occurring polysaccharides as well as polysaccharides that are obtained via chemical synthesis or genetic engineering. The term is used to include disaccharides, oligosaccharides and longer saccharide polymers, wherein the individual monomeric saccharide units may be naturally occurring or modified. Modified saccharides include those wherein one or more of the hydroxyl groups are replaced with halogen, aliphatic groups, or are functionalized as ethers, amines, phosphates, or the like. Intersugar linkages within the polysaccharide structure may be $\alpha$-1,2,$\alpha$-1,3,$\alpha$-1,4,$\alpha$-1,6,$\beta$-1,2,$\beta$-1,3,$\beta$-1,4,$\beta$-1,6 linkages, or the lik By the terms "effective amount" or "pharmaceutically effective amount" of an agent as provided herein are meant a nontoxic but sufficient amount of the agent to provide the desired therapeutic effect. As will be pointed out below, the exact amount required will vary from subject to subject, depending on age, general condition of the subject, the severity of the condition being treated, and the particular active agent administered, and the like. An appropriate "effective" amount in any individual case may be determined by one of ordinary skill in the art by reference to the pertinent texts and literature and/or using routine experimentation.

By "pharmaceutically acceptable" is meant a carrier comprised of a material that is not biologically or otherwise undesirable.

The term "transmembrane" refers to the passage of a substance into or through a body membrane, e.g., a mucosal membrane such as the gastrointestinal, sublingual, buccal, nasal, pulmonary, vaginal, corneal, or ocular membranes, so as to achieve a desired therapeutic or prophylactic effect.

The terms "absorption" and "transmembrane absorption" as used herein refer to the rate and extent to which a substance passes through a body membrane. The present dosage forms have enhanced "transmembrane absorption" as compared with hydrophilic drug administration without a bile salt or bile acid and at least one surfactant.

The term "controlled release" is intended to refer to any drug-containing formulation in which the manner and profile of drug release from the formulation are controlled. The term "controlled release" refers to immediate as well as nonimmediate release formulations, with nonimmediate release formulations including but not limited to sustained release and delayed release formulations.

The term "delayed release" is used in its conventional sense to refer to a delay in release of a composition from a dosage form following oral administration, such that the majority of the composition is released in the lower GI tract. After the dosage form reaches the intended release site, there may or may not be a further mechanism controlling the release of the composition from the dosage form. "Delayed release" may thus be an immediate release of all the contents of a drug dosage form, or it may involve controlled release in a sustained manner (as when an osmotic device is employed) or in a staged or pulsatile fashion (e.g., when a multi-component device is utilized), wherein the term "sustained" means that release occurs during an extended time period, and the terms "staged" and "pulsatile" mean that release occurs in two or more spaced apart pulses.

"Enteric coating" or "enterically coated" as used herein relates to the presence of polymeric materials in a drug formulation that enable targeting of the released hydrophilic drug to a particular location within the body, generally at a region in the lower gastrointestinal tract.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

Accordingly, the present invention provides a practical, effective, stable and non-invasive oral dosage form that is designed to be relatively insensitive to physiological effects (dilution, pH, food), capable of delivering effective levels of enhancing compositions containing a bile salt or acid in a delayed release fashion to a target site within the body, and capable of making use of the enormous absorbing surface of the intestinal tract to improve the absorption enhancing index (i.e., the ratio of enhancement efficacy to toxicity), thus improving the safety and efficacy of the pharmaceutical composition. The present invention, wherein a hydrophilic drug is delivered with an appropriate amount of an enhancing composition to an appropriate site, at an effective and consistent rate, effectively provides therapeutically active blood levels of the active agent.

The present dosage forms are delayed release in nature, such that the release of composition from the dosage form is delayed after oral administration, and preferably occurs in the lower GI tract. After reaching the intended release site, there may or may not be a further mechanism controlling release of the composition from the dosage form. That is, delayed release of the composition from the dosage form may be immediate and substantially complete at the intended release site, or, alternatively, release at the intended site may occur in a sustained fashion over an extended period of time, or in a staged or pulsatile fashion.

The performance of the delayed release dosage form is not dependent on the pH of the lower GI tract where the active agent is absorbed. For certain enhancer components, e.g., bile salts and ionizable surfactants, pH plays a critical role in affecting the solubility, permeability, and aggregation state of a composition's components. The changes in the physicochemical and biochemical properties of the molecular entities present in a composition or dosage form may in turn affect the performance of the composition or dosage form. Therefore, it is preferred that the fluctuation of pH in the small intestine caused, for example, by the release of acidic stomach, not adversely affect the absorption or the bioavailability of the active agent. The performance of the present. compositions and dosage forms does not depend on an artificial manipulation of the pH of the gut.

II. The Active Agent

The active agent is a hydrophilic drug that generally has an aqueous solubility greater than about 100 $\mu$g/ml. Such drugs include polysaccharides and other macromolecular drugs such as peptides, proteins, peptidomimetics, cytokines, nucleotides, nucleosides, genetic materials, toxoids, serum vaccines, etc. Generally, the hydrophilic drug is a polysaccharide drug, e.g., a disaccharide, oligosaccharide, or longer chain saccharide polymer that is suitable for administration to a human being. Examples of polysaccharide drugs include, without limitation, glucosamine, glycosaminoglycans, dextran, xylan, pentasaccharide, polygalacturonic acid, polymannuronic acid, chitin, pharmaceutically acceptable salts, esters or other derivatives thereof, and combinations of any of the foregoing. That is, a single polysaccharide drug may be administered, or two or more polysaccharide drugs may be administered in combination. The polysaccharide drugs may also be fragments of naturally occurring or synthetic polysaccharides.

Preferred polysaccharide drugs are glycosaminoglycans selected from heparin, heparan, chondroitin, dermatan, hyaluronic acid and pharmaceutically acceptable salts and esters thereof. More preferred polysaccharide drugs for administration using the present dosage forms and delivery systems are heparin, low molecular weight heparin, heparan, heparin and heparan salts formed with metallic cations (e.g., sodium, calcium or magnesium, preferably sodium) or organic bases (e.g., diethylamine, triethylamine, triethanolamine, etc.), heparin and heparan esters, heparin and heparan fatty acid conjugates, heparin and heparan bile acid conjugates, heparin sulfate, and heparan sulfate. For convenience, the aforementioned more preferred polysaccharide drugs are collectively referred to herein as "heparin." The particularly preferred drug herein is low molecular weight heparin, i.e., a heparin fragment generally having a weight average molecular weight in the range of 1000 to 10,000 D. Examples of low molecular weight heparin fragments include, but are not limited to, enoxaparin, dalteparin, danaproid, gammaparin, nadroparin, ardeparin, tinzaparin, certoparin and reviparin.

The active agent in the present dosage forms may be an integral part of the composition, or it may be presented in a coating on the dosage form, e.g., on a capsule, tablet, or caplet, or on each of a plurality of granules, beads, or pellets. In preferred embodiments, the active agent, e.g., low molecular weight heparin, is present as a part of the coating on the dosage form. Alternatively, the active agent is present as an integral part of the composition and is at least partially solubilized or suspended therein. The active agent may take any number of physical forms, e.g., it may be in crystalline, amorphous, nanosized, micronized or milled form.

It may be desirable to include one or more additional active agents in the dosage forms herein. A wide range of additional active agents may be co-administered with the hydrophilic drug, including both hydrophilic and lipophilic active agents, particularly although not necessarily agents that potentiate certain effects of the hydrophilic drug, or vice versa. For example, co-administration with aspirin would be desirable to treat unstable angina, and co-administration with warfarin would be indicated for prophylaxis of deep-vein thrombosis.

III. The Absorption Enhancing Composition

The invention involves in one embodiment the delivery of a hydrophilic drug with an enhancing composition comprised of a bile salt or bile acid, at least one surfactant selected from the group consisting of hydrophilic surfactants, lipophilic surfactants, and optionally additional components and excipients, with a solubilizer representing a particularly preferred additional component. The hydrophilic drug is preferably although not necessarily admixed with the enhancing composition in a single dosage form, e.g., in a formulation contained within an enterically coated capsule.

A. The Bile Salt or Bile Acid

As well known in the art, bile acids are naturally occurring surfactants having a nucleus derived from cholanic acid and are substituted with a 3α-hydroxyl group and optionally with other hydroxyl groups as well, typically at the $C_6$, $C_7$ or $C_{12}$ position of the sterol nucleus. Bile acids include, for example, cholic acid, deoxycholic acid, lithocholic acid, chenodeoxycholic acid (also referred to as "chenodiol" or "chenic acid"), and ursodeoxycholic acid. The aforementioned acids are "unconjugated" bile acids in that the carboxyl group extending from the $C_{17}$ position of the sterol nucleus is in free acid form. Bile acids may also be "conjugated," typically by reaction of the aforementioned carboxyl group with the free amine moiety of glycine ($H_2NCH_2COOH$) or taurine ($H_2NCH_2CH_2SO_3H$) to form a peptide linkage. Conjugated bile acids thus include, for example, taurocholic acid, taurodeoxycholic acid, taurolithocholic acid, taurochenodeoxycholic acid, tauroursodeoxycholic acid, glycocholic acid, glycodeoxycholic acid, glycolithocholic acid, glycochenodeoxycholic acid, and glycoursodeoxycholic acid. Any of the aforementioned bile acids can be advantageously used in conjunction with the present invention. The bile acids may also be in the form of a salt, in which case the acidic functionality is ionized and associated with a cationic counter-ion, e.g., sodium, potassium, ammonium, or the like. In addition, the bile acids herein may be in the form of a choleic acid, wherein a bile acid forms a coordination complex with another compound, typically although not necessarily a fatty acid.

Particularly preferred bile acids for use herein are ursodeoxycholic acid and chenodeoxycholic acid, and when used in the salt form, the sodium salt is particularly preferred.

It will be appreciated by those of skill in the art that bile "acids" and bile "salts herein are interchangeable, in that the form of the compound will depend on the pH of the surrounding environment. That is, at lower pH, a bile acid will be in the form of the free acid, while at higher pH, the salt form will predominate.

The bile salt or acid in the present dosage forms may be an integral part of the absorption enhancing composition, or it may represent a coating on a dosage form, e.g., on a capsule, tablet, or caplet, or on each of a plurality of granules, beads, or pellets. It is preferred, however, that the bile acid or bile salt represent an integral part of the absorption-enhancing composition and be at least partially solubilized or suspended therein. The bile salt or acid may take any number of physical forms, e.g., it may be in crystalline, amorphous, nanosized, micronized or milled form.

B. Surfactants

The surfactant is selected from the group consisting of hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant will generally have an HLB value of at least 10, while suitable lipophilic surfactants will generally have an HLB value of or less than about 10. As is well known in the art, however, the terms "hydrophilic" and "lipophilic" are relative terms. To function as a surfactant, a compound must necessarily include polar or charged hydrophilic moieties as well as non-polar lipophilic (hydrophobic) moieties; that is, a surfactant compound must be amphiphilic. An empirical parameter commonly used to characterize the relative hydrophilicity and hydrophobicity of non-ionic amphiphilic compounds is the hydrophilic-lipophilic balance (" HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. It should be appreciated that the HLB value of a surfactant is merely a rough guide generally used to enable formulation of industrial, pharmaceutical and cosmetic emulsions. For many surfactants, including several polyethoxylated surfactants, it has been reported that HLB values can differ by as much as about 8 HLB units, depending upon the empirical method chosen to determine the HLB value; see, e.g., Schott (1990) *J Pharm. Sci.* 79(1):87–88. Likewise, for certain polypropylene oxide-containing block copolymers (e.g., the Pluronic® surfactants, from BASF Corp.), the HLB values may not accurately reflect the true physical chemical nature of the compounds. Finally, commercial surfactant products are generally not pure compounds, but are complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify hydrophilic and lipophilic surfactants for use in conjunction with the present invention.

1. Hydrophilic Surfactants

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: the ionized from a surfactant selected from the group consisting of: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

More preferred ionic surfactants are the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Preferred hydrophilic non-ionic surfactants include alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof.

More preferably, the hydrophilic non-ionic surfactant is selected from the group consisting of polyethylene glycol sorbitan fatty acid esters and hydrophilic transesterification products of a polyol with at least one member of the group consisting of triglycerides, vegetable oils, and hydrogenated vegetable oils. The polyol is preferably glycerol, ethylene glycol, polyethylene glycol, sorbitol, propylene glycol, pentaerythritol, or a saccharide.

Particularly preferred hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Among these preferred non-ionic surfactants, more preferred are PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20, polysorbate 80, POE-9 lauryl ether, POE-23 lauryl ether, POE-10 oleyl ether, PEG-24 cholesterol, sucrose monostearate, sucrose monolaurate and poloxamers. Most preferred are PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 80, tocopheryl PEG-1000 succinate, PEG-24 cholesterol, and hydrophilic poloxamers.

2. Lipophilic Surfactants

Suitable lipophilic surfactants include, by way of example: fatty alcohols; glycerol fatty acid esters; acetylated glycerol fatty acid esters; lower alcohol fatty acids esters;

propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Among the lipophilic transesterification products, most preferred are transesterification products of a polyol such as ethylene glycol, glycerol, propylene glycol, and sorbitol. As is known in the art, a large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, maltol, sorbitol, and pentaerythritol. Among these alcohol-oil transesterified surfactants, preferred hydrophobic surfactants include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® M 2735 CS), PEG-8 corn oil (Labrafil® M WL 2609 BS), PEG-20 corn glycerides (Crovol M40), and PEG-20 almond glycerides (Crovol A40).

Still other suitable surfactants will be apparent to those skilled in the art, and/or are described in the pertinent texts and literature, and/or are set forth in the parent application hereto, U.S. Ser. No. 09/375,636, incorporated by reference herein.

C. Solubibizers

In a preferred embodiment, the absorption enhancing composition further includes a solubilizer to ensure good solubilization and/or dissolution of the bile salt or acid, and to minimize precipitation of the bile salt or acid. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following:

alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives;

ethers of polyethylene glycols having an average molecular weight of about 200 to about 6000, such as tetrahydrofurfuryl alcohol PEG ether (glycofurol, available commercially from BASF under the trade name Tetraglycol®) or methoxy PEG (Union Carbide);

amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone;

esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Preferred solubilizers include triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. Of course, when the dosage forms are ultimately administered to a patient, the amount of a given solubilizer is limited to a bioacceptable amount, which may be readily determined by one of skill in the art. In some circumstances, it may be advantageous to include amounts of solubilizers far in excess of bioacceptable amounts, for example to maximize the concentration of the hydrophilic drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the hydrophilic drug, the bile salt or bile acid, and the surfactant. If desired, very small amounts of solubilizer may also be used, such as 5%, 2%, 1% or even less. Typically, the solubilizer will be present in an amount of about 1% to about 100%, more typically about 5% to about 25% by weight.

D. Additives and Excipients

In addition to the bile salt or acid and surfactant, the absorption enhancing composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris (hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Preferred cations include sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

When the hydrophilic therapeutic agent is subject to enzymatic degradation, the present compositions can also include an enzyme inhibiting agent. Enzyme inhibiting agents are shown for example, in Bemskop-Schnurch (1998), "The use of inhibitory agents to overcome enzymatic barrier to perorally administered therapeutic peptides and proteins," *J. Controlled Release* 52:1–16.

Generally, inhibitory agents can be divided into the following classes:

- inhibitors that are not based on amino acids, such as P-aminobenzamidine, FK-448, camostat mesylate and sodium glycocholate;
- amino acids and modified amino acids, such as aminoboronic acid derivatives and n-acetylcysteine;
- peptides and modified peptides, such as bacitracin, phosphinic acid dipeptide derivatives, pepstatin, antipain, leupeptin, chymostatin, elastatin, bestatin, hosphoramindon, puromycin, cytochalasin potatocarboxy peptidase inhibitor, and amastatin;
- polypeptide protease inhibitors, such as aprotinin (bovine pancreatic trypsin inhibitor), Bowman-Birk inhibitor and soybean trypsin inhibitor, chicken egg white trypsin inhibitor, chicken ovoinhibitor, and human pancreatic trypsin inhibitor;
- complexing agents, such as EDTA, EGTA, 1,10-phenanthroline and hydroxychinoline; and
- mucoadhesive polymers and polymer-inhibitor conjugates, such as polyacrylate derivatives, chitosan, cellulosics, chitosan-EDTA, chitosan-EDTA-antipain, polyacrylic acid-bacitracin, carboxymethyl cellulose-pepstatin, polyacrylic acid-Bowman-Birk inhibitor.

The choice and levels of the enzyme inhibitor are based on toxicity, specificity of the proteases and the potency of inhibition. The inhibitor can be suspended or solubilized in the composition preconcentrate, or added to an aqueous diluent or as a beverage.

Without wishing to be bound by theory, it is believed that an inhibitor can finction solely or in combination as: a competitive inhibitor, by binding at the substrate binding site of the enzyme, thereby preventing the access to the substrate (examples of inhibitors believed to operate by this mechanism are antipain, elastatinal and the Bowman Birk inhibitor); a non-competitive inhibitor that can be simultaneously bound to the enzyme site along with the substrate, as their binding sites are not identical; and/or a complexing agent due to loss in enzymatic activity caused by deprivation of essential metal ions out of the enzyme structure.

E. Optimization of Component Amounts

In general, it is important that the composition include sufficient amounts of the bile salt or acid and surfactant(s) and in appropriate ratios to provide a therapeutically meaningful enhancement in the rate, extent and consistency of transmembrane absorption of the hydrophilic drug. Typically, the amount of bile salt or acid in the composition or dosage form should be about 1% to 50% by weight, preferably about 5% to 20%, based on the total weight of the pre-concentrate composition. Also, the amount of surfactant(s) in the composition or dosage form should be about 5% to 80% by weight, preferably about 15% to 50%, based on the total weight of the pre-concentrate composition. In a preferred embodiment wherein a mixture of hydrophilic surfactant(s) and lipophilic surfactant(s) are present, the ratio of the hydrophilic surfactant(s) to the lipophilic surfactant(s) is about 0.1 to 10 (w/w).

The amount of solubilizer that can be included is not particularly limited. Of course, when the dosage forms are ultimately administered to a patient, the amount of a given solubilizer is limited to a bioacceptable amount, which may be readily determined by one of skill in the art. In some circumstances, it may be advantageous to include amounts of solubilizers far in excess of bioacceptable amounts, for example to maximize the concentration of the hydrophilic drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the hydrophilic drug, the bile salt or bile acid, and the surfactant. If desired, very small amounts of solubilizer may also be used, such as 5%, 2%, 1% or even less. Typically, the solubilizer will be present in an amount of about 1% to about 100%, more typically about 5% to about 25% by weight.

In one preferred embodiment, the components of the dosage form are present in amounts such that upon dilution with an aqueous medium, a substantially homogeneous aqueous dispersion is formed that preferably has a relatively small particle size, ideally much smaller than the larger particles characteristic of vesicular or emulsion phases. This reduced particle size enables more efficient transport through the intestinal aqueous boundary layer, and through the absorptive brush border membrane. More efficient transport to absorptive sites leads to improved and more consistent absorption of the active agent.

The aqueous dispersion formed upon dilution of the present composition with an aqueous medium is substantially optically clear as a reflection of the aforementioned optimal particle size. The composition in the pre-concentrate form, ie., before dilution with an aqueous medium, need not be clear, as it is the clarity upon dilution with an aqueous medium that is preferred. The dilution can be in vitro or in vivo, and optical clarity should be assessed at dilutions of about 5 to 250-fold or more, preferably about 10 to 100-fold, as is encountered in the gastrointestinal environment. It should be appreciated that when the desired dosage form includes an amount of the hydrophilic drug that is suspended, but not solubilized, in the composition, the appropriate concentrations of the bile acid or salt and the surfactant(s) should be determined by the optical clarity of the diluted composition without the therapeutic agent. It also should be appreciated that when the desired dosage form includes additives, such as colorants and water-insoluble materials including talc, wax, magnesium stearate, titanium oxide, certain polymers, etc., that contribute significant absorbance or turbidity, the appropriate concentrations of the bile acid or salt and the surfactant(s) should be determined by the optical clarity of the diluted composition without the water-insoluble additive.

In this preferred embodiment, the relative amounts of the components are readily determined by observing the properties of the resultant dispersion; i.e., when the relative amounts of the bile salt or acid and surfactant(s) are within the preferred range, the resultant aqueous dispersion is optically clear. When the relative amounts are outside the preferred range, the resulting dispersion is visibly cloudy, resembling a conventional emulsion or multiple-phase system. The optical clarity of the aqueous dispersion can be measured using standard quantitative techniques for turbidity assessment. One convenient procedure to measure turbidity is to measure the amount of light of a given wavelength transmitted by the solution, using, for example, a UV-visible spectrophotometer. Using this measure, optical clarity corresponds to high transmittance, since cloudier solutions will scatter more of the incident radiation, resulting in lower transmittance measurements. If this procedure is used, care should be taken to ensure that the composition itself does not absorb light of the chosen wavelength, as any true absorbance necessarily reduces the amount of transmitted light and falsely increases the quantitative turbidity value. In the absence of chromophores at the chosen wavelength, e.g. 400 nm, suitable dispersions at a dilution of 100× (i.e., at an aqueous solution to composition ratio of about 100:1) should have an apparent absorbance of less than about 0.3, preferably less than about 0.2, and more preferably less than about 0.1.

Other methods of characterizing optical clarity known in the art may also be used, and any or all of the available methods may be used to ensure that the resulting aqueous dispersions possess the preferred optical clarity.

Alternatively, the amounts of the bile salt or bile acid and the surfactant(s) can be readily determined by the average particle size of the aqueous dispersion form from the composition upon dilution in an aqueous medium. These particle sizes can be measured at dilution amounts of 5 to 250-fold or more, preferably about 10 to about 100-fold, as is typical of the dilution expected in the gastrointestinal tract. Preferably, the average particle size is less than about 200 nm, more preferably less than about 100 nm, still more preferably less than about 50 nm and most preferably less than about 20 nm. A preferred method of assessing the appropriate amount of each component is to quantitatively measure the size of the particles of which the dispersion is composed. These measurements can be performed on commercially available particle size analyzers, such as, for example, a Nicomp particle size analyzer available from Particle Size Systems, Inc., of Santa Barbara, Calif. Using this measure, aqueous dispersions according to the present invention that have optimal average particle sizes can be prepared. Similarly, care should be taken to discount the particles contributed by the additives. It is desirable that the average particle size be less than about 200 nm, preferably less than about 100, more preferably less than about 50 nm, still more preferably less than about 30 nm, and most preferably less than about 20 nm. It is also preferred although not essential that the particle size distribution be substantially monomodal.

F. Other Aspects of the Composition

In preferred embodiments, the present pharmaceutical compositions and dosage forms are substantially triglyceride-free. The term "triglyceride" as used herein refers to glycerol triesters of $C_6$ to about $C_{25}$ fatty acids. As used herein, the term "substantially triglyceride-free" means compositions which contain triglycerides, if at all, only as minor components or impurities in surfactant mixtures. Thus, it should be appreciated that the present invention does not exclude the use of surfactant products that contain small amounts of triglycerides as impurities or as unreacted starting material. It is expected that commercial mixtures suitable for use in the present invention may contain as much as 5% triglycerides by weight as unintended components. Thus, "substantially triglyceride-free" should be understood as meaning free of added triglycerides, and containing less than 5%, preferably essentially 0%, triglyceride impurities.

The lack of triglycerides provides pharmaceutical compositions that are not dependent upon lipolysis, and upon the many poorly characterized factors that affect the rate and extent of lipolysis, for effective presentation of an active agent or other component of the composition to an absorptive site. Such factors include the presence of composition components that may inhibit lipolysis; patient conditions that limit production of lipase, such as pancreatic lipase secretory diseases; and dependence of lipolysis on stomach pH, endogenous calcium concentration, and presence of co-lipase or other digestion enzymes. The lack of lipolysis dependence further provides transport, which is less prone to suffer from any lag time between administration and absorption caused by the lipolysis process, enabling a more rapid onset of therapeutic action and better bioperformance characteristics once the absorption enhancing composition is released within a patient's body at the intended release site, i.e., the lower GI tract. In addition, the compositions of the present invention can make use of hydrophilic surfactants that might otherwise be avoided or limited due to their potential lipolysis inhibiting effects.

In addition, the compositions and dosage forms of the invention are in a preferred embodiment completely or substantially nonaqueous. By "substantially nonaqueous" is meant that the composition or dosage form contains less than 20% water (v/v). More preferably, the composition contains less than about 10% water and most preferably less than about 5% water. In turn, this means that any water present will not form a continuous aqueous phase.

The lack of water provides for improved stability and compatibility in contexts wherein a significant amount of water could be problematic in these respects. For example, numerous active agents or excipients are prone to hydrolysis. In addition, certain excipients may undergo phase changes, such as precipitation and gelation, in the presence of a significant amount of water, thus altering or losing the intended. Also, significant amounts of water may not be compatible with certain dosage forms such as gelatin capsules. Although a small amount of water is present in gelatin capsule shells to prevent cracking or brittleness of the capsules, a large amount of water may cause softening, dissolving, leaking or breaking of the capsules during storage.

IV. Dosage Forms

In a preferred embodiment, the bile salt or acid, the surfactant(s) and the hydrophilic drug are present in a single dosage form. Alternatively, the bile salt or acid and the surfactant may be provided in one dosage form, and the drug will be administered separately. The dosage form(s) are not limited with respect to size, shape or general configuration, and may comprise, for example, a capsule, a tablet or a caplet, or a multiparticulate carrier comprising a plurality of particles, granules, beads, pellets, or mixtures thereof, that may or may not be encapsulated. Furthermore, either the drug or the bile salt or bile acid may be present as a coating. In addition, the dosage form or components of the dosage form may be enterically coated; for example, a capsule may be enterically coated and/or drug-containing beads contained therein may be enterically coated. Preferred dosage forms have an enteric coating suitable for providing the desired delayed release profile.

The compositions and dosage forms can be processed and prepared according to conventional techniques known to those skilled in the art, such as lyophilization, encapsulation, compression, melting, extrusion, balling, drying, chilling, molding, spraying, spray congealing, coating, comminution, mixing, homogenization, sonication, cryopelletization, spheronization, and granulation, to produce the desired dosage form. Processing techniques such as size reduction, co-precipitation, coacervation, lyophilizing, spray drying, eutectic mixing and solid solutioning are particularly useful for making the bile salt or acid more amenable to rapid dissolution.

The dosage form is delayed release in nature, as noted previously. The specific delayed release profile can be readily altered by employing a polymeric matrix composition, a coated matrix composition, a multiparticulate composition, a coated multiparticulate composition, an ion-exchange resin-based composition, an osmosis-based composition, or a biodegradable polymeric composition. Materials suitable for preparing such delayed release dosage forms are known in the art, and include, for example, insoluble plastics (e.g., polyvinyl chloride or polyethylene), hydrophilic polymers (generally selected from the enteric coating materials described infra), and fatty compounds (e.g., glyceryl tristearate and waxes such as carnauba wax). Without wishing to be bound by theory, it is believed that the release may be effected through favorable diffusion, dissolution, erosion, ion exchange, osmosis or combinations thereof.

However, preferred dosage forms are enterically coated. The enteric coating provides a means for delaying release of the absorption enhancing composition, including the active agent, such that the composition can be predictably released in the lower GI tract without excessive dilution. The enteric coating also prevents unnecessary exposure of the composition, including the active agent, to the epithelial and mucosal tissue of the buccal cavity, pharynx, esophagus and stomach, and to the enzymes associated with these tissues, thus protecting the active agents and other components of the composition and dosage form from degradation or binding. Furthermore, delayed release also reduces the likelihood of irritation or damage to the aforementioned tissues, allowing for a safer delivery approach. Accordingly, enterically coated dosage forms allow optimization of drug absorption, active agent protection and safety. Multiple enteric coatings targeted to release the active agent at various regions in the lower GI tract may also be used.

The enteric coating is typically although not necessarily a polymeric material. Preferred enteric coating materials comprise bioerodible, gradually hydrolyzable and/or gradually water-soluble polymers. The "coating weight," or relative amount of coating material per dosage form, generally dictates the time interval between ingestion and drug release. Any coating material should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery of the active to the lower gastrointestinal tract. The selection of the specific enteric coating material will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; ease of application as a coating; and economical practicality.

Suitable enteric coating materials include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the tradename "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Combinations of different coating materials may also be used to coat a single capsule. A particularly preferred enteric coating material for use herein are those acrylic acid polymers and copolymers available under the tradename "Eudragit" from Rohm Pharma (Germany). The Eudragit series E, L, S, RL, RS and NE copolymers are available as solubilized in organic solvent, in an aqueous dispersion, or as a dry powder. The Eudragit series RL, NE, and RS copolymers are insoluble in the gastrointestinal tract but are permeable and are used primarily for extended release. The Eudragit series E copolymers dissolve in the stomach. The Eudragit series L, L-30D and S copolymers are insoluble in stomach and dissolve in the intestine, and are thus most preferred herein.

A particularly suitable methacrylic copolymer is Eudragit L, particularly L-30D, and Eudragit 100-55. In Eudragit L-30D, the ratio of free carboxyl groups to ester groups is approximately 1:1. Further, the copolymer is known to be insoluble in gastrointestinal fluids having pH below 5.5, generally 1.5–5.5, i.e., the pH generally present in the fluid of the upper gastrointestinal tract, but readily soluble or partially soluble at pH above 5.5, i.e., the pH generally present in the fluid of lower gastrointestinal tract. Another particularly suitable methacrylic acid polymer is Eudragit S, which differs from Eudragit L-30D in that the ratio of free carboxyl groups to ester groups is approximately 1:2. Eudragit S is insoluble at pH below 5.5, but unlike Eudragit L-30D, is poorly soluble in gastrointestinal fluids having a pH in the range of 5.5 to 7.0, such as in the small intestine. This copolymer is soluble at pH 7.0 and above, i.e., the pH generally found in the colon. Eudragit S can be used alone as a coating to provide drug delivery in the large intestine. Alternatively, Eudragit S, being poorly soluble in intestinal fluids below pH 7, can be used in combination with Eudragit L-30D, soluble in intestinal fluids above pH 5.5, in order to provide a delayed release composition, which can be formulated to deliver the active agent to various segments of the intestina tract. The more Eudragit L-30D used, the more proximal release and delivery begins, and the more Eudragit S used, the more distal release and delivery begins. It will be appreciated by those skilled in the art that both Eudragit L-30D and Eudragit S can be replaced with other pharmaceutically acceptable polymers having similar pH solubility characteristics.

The enteric coating provides for controlled release of the active agent, such that drug release can be accomplished at some generally predictable location in the lower intestinal tract below the point at which drug release would occur without the enteric coating. The enteric coating also prevents exposure of the hydrophilic therapeutic agent and carrier to the epithelial and mucosal tissue of the buccal cavity, pharynx, esophagus, and stomach, and to the enzymes associated with these tissues. The enteric coating therefore helps to protect the active agent and a patient's internal tissue from any adverse event prior to drug release at the desired site of delivery. Furthermore, enteric coated dosage forms allow optimization of drug absorption, active agent protection, and safety. Multiple enteric coatings targeted to release the active agent at various regions in the lower gastrointestinal tract would enable even more effective and sustained improved delivery throughout the lower gastrointestinal tract.

The coating can, and usually does, contain a plasticizer to prevent the formation of pores and cracks that would permit the penetration of the gastric fluids. Suitable plasticizers include, but are not limited to, triethyl citrate, triacetin (glyceryl triacetate), acetyl triethyl citrate, Carbowax 400 (polyethylene glycol 400), diethyl phthalate, tributyl citrate, acetylated monoglycerides, glycerol, fatty acid esters, propylene glycol, and dibutyl phthalate. In particular, a coating comprised of an anionic carboxylic acrylic polymer will usually contain approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The coating can be applied to the dosage form using conventional coating methods and equipment. For example, an enteric coating can be applied to a capsule using a coating pan, an airless spray technique, fluidized bed coating equipment, or the like. Detailed information concerning materials, equipment and processes for preparing coated dosage forms may be found in Pharmaceutical *Dosage Forms: Tablets*, eds. Lieberman et al. (New York: Marcel Dekker, Inc., 1989), and in Ansel et al., *Pharmaceutical Dosage Forms and Drug Delivery Systems*, 6th Ed. (Media, Pa.: Williams & Wilkins, 1995). The coating thickness, as noted above, must be sufficient to ensure that the oral dosage form remains intact until the desired site of topical delivery in the lower intestinal tract is reached.

A preferred dosage form is an enterically coated capsule for oral administration. The capsule material may be either hard or soft, and as will be appreciated by those skilled in the art, typically comprises a tasteless, easily administered and water soluble compound such as gelatin, starch or a cellulosic material. The capsules are preferably sealed, such as with gelatin bands or the like. See, for example, *Remington: The Science and Practice of Pharmacy*, Nineteenth Edition (Easton, Pa.: Mack Publishing Co., 1995), which describes materials and methods for preparing encapsulated pharmaceuticals. The formulations of the invention, comprised of a hydrophilic drug, a bile salt or acid, and at least one surfactant, are unexpectedly quite compatible with soft gelatin capsules. As is known in the art, use of soft gelatin capsules places a number of limitations on the formulations that can be encapsulated, with respect to pH, particle size, and other factors. See, for example, Ebert (1978), "Soft Elastic Gelatin Capsules: A Unique Dosage Form," *Pharmaceutical Technology* 1(5). In this embodiment, the encapsulated composition may be liquid or semi-solid (e.g., a gel), and may comprise the drug, the bile salt or acid, and the surfactant(s). Alternatively, or in addition, the bile salt or acid and/or the drug may be present as a coating on the capsule, under the enteric coating. The encapsulated composition may also be in the form of granules, beads or pellets, which may or may not be similarly coated with the bile salt or acid, the drug, and/or the enteric coating.

The delayed release dosage form may further comprise one or more layers of a protective coating, typically although not necessarily representing the outermost layer of the dosage form, serving to seal the dosage form and thereby minimize exposure to the outside environment where moisture and other factors can have adversely. The protective coating can also be beneath the enteric coating and/or other coatings, e.g., coatings containing the active agent or the bile salt or bile acid. Physical separation of discrete regions of the dosage form can increase the stability of the dosage form when individual coatings or components are not compatible with each other. For example, an intermediate protective coating can physically separate an acid-labile active agent or excipient from an enteric coating polymer containing acidic groups, e.g. free carboxyl groups, which can otherwise cause degradation of the acid-labile material during the coating process or during storage.

The protective coating can comprise one or more water-soluble inert layers, optionally containing pH-buffering agents. The coating(s) can be applied to the composition or the dosage form by conventional coating procedures as described earlier with respect to enteric coatings, and may contain additives and excipients as also described above. Suitable protective coating materials are comprised of pharmaceutically acceptable, water-soluble, inert materials typically used for film-coating applications. For example, the coating material may be sugar, polyethylene glycol, polyvinylpyrrolidone, polyvinyl alcohol, hydroxypropyl cellulose, methylcellulose, hydroxymethyl cellulose, hydroxypropyl methylcellulose, or the like. Additives, such as plasticizers, colorants, pigments, fillers, anti-tacking and anti-static agent may also be included. Examples of specific additives include magnesium stearate, titanium oxide, talc and mixtures thereof.

In another embodiment, drug dosage forms are provided that comprise an osmotically activated device (e.g., an osmotically activated capsule or tablet) housing the bile salt or acid, the surfactant(s), and the hydrophilic drug. Preferably, although not necessarily, the osmotically activated device is enterically coated. The components of the internal, drug-containing formulation are as described above with respect to enterically coated capsules; however, conventional solid carriers can be used as well as the liquid and semi-solid carriers described above.

In this embodiment, the drug-containing formulation is encapsulated in a semipermeable membrane or barrier containing a small orifice. As known in the art with respect to so-called "osmotic pump" drug delivery devices, the semipermeable membrane allows passage of water in either direction, but not drug (or other components of the composition). Therefore, when the device is exposed to aqueous fluids, water will flow into the device due to the osmotic pressure differential between the interior and exterior of the device. The flow rate of water into the device, dV/dt, can be represented as $$(kA/h)(\Delta\pi-\Delta P)$$

wherein k is the permeability of the membrane, A is the area of the membrane, h is the thickness of the membrane, $\Delta\pi$ is the osmotic pressure differential, and $\Delta P$ is the hydrostatic pressure differential. With a sufficiently large orifice, the osmotic pressure will be far greater than the hydrostatic pressure differential, so that the flow rate of water into the device may be represented simply as $$(kA/h)(\Delta\pi).$$

As water flows into the device, the drug-containing formulation in the interior will be "pumped" out through the orifice. The rate of drug release dD/dt, will be equivalent to the inflow rate of water times the drug concentration.

Suitable materials for the semipermeable membrane include, but are not limited to, polyvinyl alcohol, polyvinyl chloride, semipermeable polyethylene glycols, semipermeable polyurethanes, semipermeable polyamides, semipermeable sulfonated polystyrenes and polystyrene derivatives; semipermeable poly(sodium styrenesulfonate), semipermeable poly(vinylbenzyltrimethylammonium chloride), and cellulosic polymers such as cellulose acetate, cellulose diacetate, cellulose triacetate, cellulose propionate, cellulose acetate propionate, cellulose acetate butyrate, cellulose trivalerate, cellulose trimellitate, cellulose tripalmitate, cellulose trioctanoate, cellulose tripropionate, cellulose disuccinate, cellulose dipalmitate, cellulose dicaprylate, cellulose acetate succinate, cellulose propionate succinate, cellulose acetate octanoate, cellulose valerate palmitate, cellulose acetate heptanoate, cellulose acetaldehyde dimethyl acetate, cellulose acetate ethylcarbamate, cellulose acetate methylcarbamate, cellulose dimethylaminoacetate and ethyl cellulose.

Enterically coated, osmotically activated devices can be manufactured using conventional materials, methods and equipment. For example, osmotically activated devices may be made by first encapsulating, in a pharmaceutically acceptable soft capsule, a liquid or semi-solid formulation of a hydrophilic drug as described previously. This interior capsule is then coated with a semipermeable membrane composition (comprising, for example, cellulose acetate and polyethylene glycol 4000 in a suitable solvent such as a methylene chloride-methanol admixture), for example using an air suspension machine, until a sufficiently thick laminate is formed, e.g., around 0.05 mm. The semipermeable laminated capsule is then dried using conventional techniques. subsequently, an orifice having a desired diameter (e.g., about 0.99 mm) is provided through the semipermeable laminated capsule wall, using, for example, mechanical drilling, laser drilling, mechanical rupturing, or erosion of an erodible element such as a gelatin plug. The osmotically activated device may then be enterically coated as previously described. For osmotically activated devices containing a solid carrier rather than a liquid or semi-solid carrier, the interior capsule is optional; that is, the semipermeable membrane may be formed directly around the carrier-drug composition. However, preferred carriers for use in the drug-containing formulation of the osmotically activated device are solutions, suspensions, liquids, immiscible liquids, emulsions, sols, colloids, and oils. Particularly preferred carriers include, but are not limited to, those described in Section IIA with respect to enterically coated capsules containing liquid or semisolid drug formulations.

V. Utility and Administration

In accordance with the present invention, administration of a hydrophilic drug may be carried out in order to treat any disorder, condition or disease for which the drug is generally indicated. Dosage regimens and daily dosage for polysaccharide drugs such as heparins and heparinoids can vary a great deal, as a number of factors are involved, including the particular heparin derivative, analog or fragment administered, the age and general condition of the patient, the particular condition or disorder and its severity, and the like. Clearly, however, it is necessary that the dosage given be sufficient to provide the desired pharmacological activity in a patient=s circulation. Typical dosages for low molecular weight heparins or heparinoids administered intravenously or subcutaneously are on the order of about 700 to 20,000 IU/day, while typical dosages for unfractionated heparin administered by injection are on the order of 10,000 to 40,000 Units/day. Expected typical dosages for orally administered low molecular weight heparin using the dosage forms of the invention are on the order of about 700 to 400,000, preferably 2,500 to 100,000 IU/day, while expected typical dosages for orally administered unfractionated heparin using the dosage forms of the invention are on the order of about 2,500 to 800,000 Units/day. For the administration of heparin and heparinoids, the indication will typically be the treatment and prevention of thrombosis.

It is to be understood that while the invention has been described in conjunction with the preferred specific embodiments thereof, that the description above as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

EXPERIMENTAL

The practice of the present invention will employ, unless otherwise indicated, conventional techniques of pharmaceutical formulation, medicinal chemistry, biological testing, and the like, which are within the skill of the art. Such techniques are explained fully in the literature. Preparation of various types of pharmaceutical formulations are described, for example, in Lieberman et al., cited supra; and Gibaldi and Perrier, Pharmacokinetics (Marcel Dekker, 1982), provides a description of the testing procedures useful to evaluate drug delivery systems such as the enterically coated dosage forms described herein.

Exemplary Compositions for Delayed Release Dosage Forms

Compositions in the following examples can be prepared as described. Weighed amounts of the components are blended together to form a homogenous mixture suitable for encapsulation, granulation, or other processing. If the active agent, e.g. low molecular weight heparin (LMW heparin), heparin sodium, or other polysaccharide drug are to be combined with these components in the dosage form, weighed amounts of active agent can be uniformly dispersed within these mixtures to achieve the desired active concentration.

| Composition | (mg) |
|---|---|
| Example 1 | |
| Enoxaparin sodium (a LMW heparin) 50 | |
| Deoxycholic acid, sodium salt | 100 |
| Incrocas 35 | 300 |
| Capryol 90 | 300 |
| Example 2 | |
| Enoxaparin sodium (a LMW heparin) | 100 |
| Ursodeoxycholic acid | 100 |
| Tween 80 | 200 |
| Sodium carbonate | 100 |
| Example 3 | |
| Enoxaparin sodium (a LMW heparin) | 150 |
| Glycodihydrofusidic acid, sodium salt | 200 |
| Eastman 9-45 | 200 |
| Propylene glycol | 200 |
| Example 4 | |
| Enoxaparin sodium (a LMW heparin) | 200 |
| Taurochenodeoxycholic acid, sodium salt | 150 |
| Phospholipids | 300 |
| Propylene glycol | 200 |
| Example 5 | |
| Dalteparin sodium (a LMW heparin) | 100 |
| Cholylsarcosine, sodium salt | 150 |
| Phospholipids | 300 |
| Linoleic acid | 200 |
| Polyethlene glycol 400 | 200 |
| Example 6 | |
| Dalteparin sodium (a LMW heparin) | 200 |
| Cholylsarcosine, sodium salt | 150 |
| Oleic acid, sodium salt | 400 |
| Cremophor RH40 | 200 |
| Example 7 | |
| Dalteparin sodium (a LMW heparin) | 300 |
| Taurocholic acid | 150 |
| Oleic acid, sodium salt | 200 |
| Lauroglycol FCC | 200 |
| Cremophor RH40 | 200 |
| Example 8 | |
| Heparin sodium | 400 |
| Glycoursodeoxycholic acid | 150 |
| Labrafil M1944CS | 200 |
| Olive oil | 100 |
| Cremophor RH40 | 300 |
| Propylene glycol | 200 |
| Example 9 | |
| Heparin sodium | 200 |
| Taurocholic acid, sodium salt | 60 |
| Arlacel 186 | 120 |
| Safflower oil | 80 |
| Cremophor RH40 | 120 |
| Propylene glycol | 120 |
| Example 10 | |
| Dextran | 100 |
| Taurodihydrofusidic acid, sodium salt | 120 |
| Sodium lauryl sulfate | 50 |
| Incrocas 35 | 300 |
| Arlacel 186 | 300 |
| Propylene glycol | 200 |
| Example 11 | |
| Enoxaprin (a LMW heparin) | 100 |
| Sodium taurocholate | 50 |

-continued

| Composition | (mg) |
|---|---|
| Glycerol monolaurate | 100 |
| Cremophor RH40 | 250 |
| PEG-150 monostearate | 270 |
| Example 12 | |
| Nadroparin Ca (a LMW heparin) | 100 |
| Ursodeoxycholic acid | 100 |
| Gelucire 40/14 | 200 |
| Example 13 | |
| Enoxaprin (a LMW heparin) | 100 |
| Chenodeoxycholic acid | 137 |
| Maisine 35-1 | 46 |
| PEG-40 monostearate | 139 |
| PEG-150 monostearate | 278 |
| Example 14 | |
| Enoxaprin (a LMW heparin) | 100 |
| Ursodeoxycholic acid, sodium salt | 200 |
| Gelucire 50/13 | 200 |

Preparation of Delayed Relese Dosage Forms:

The preparation of the delayed released dosage forms of the present invention is illustrated in the following examples.

EXAMPLE 15

A pharmaceutical dosage form is prepared containing the composition of EXAMPLE in a capsule, which is then coated with an enteric coating. The composition is prepared by blending components to form a dispersion of low molecular weight heparin (LMW heparin) and sodium deoxycholate in the liquid Incrocas 35/Capryol 90 mixture. This composition is filled in capsules and coated with an enteric coating as follows.

Cellulose acetate phthalate (CAP) powder, NF is dissolved in acetone to achieve a final solids content of 11%. Triacetin is added as a plasticizer (20% w/w polymer). Capsules are dipped briefly in the CAP/triacetin solution and dried in air at room temperature. The capsule are dipped and dried repeatedly until a coating weight of ~10% (dissolution pH range of about 5.5–6.5 is achieved).

EXAMPLE 16

A pharmaceutical dosage form is prepared containing the composition of EXAMPLE 2. In this dosage form the LMW heparin and hydrophilic surfactant are encapsulated, then coated with the ursodeoxycholic acid/sodium carbonate mixture, then with a protective coating, then with an enteric coating.

The LMW heparin is dispersed in Tween 80 and filled into capsules. For the bile acid/sodium carbonate coating, ursodeoxycholic acid and sodium carbonate are dispersed in ethanol and spray coated on the capsules in a conventional coating pan to a coating weight of 106 mg/capsule. A protective coating of hydroxypropyl methylcellulose (HPMC) 603:PEG 6000:talc 4:1:4 ratio is then applied to a coating weight of ~40 mg/capsule. Finally, an enteric coating is applied using methacrylic acid/methacrylate copolymer aqueous dispersion (Eudragit L30- D55) with triethyl citrate (20%wlw copolymer) as plasticizer. Final enteric coating weight is about 70 mg.

EXAMPLE 17

A pharmaceutical dosage form is prepared containing the composition of EXAMPLE 9. In this dosage form the bile salt, surfactants, and solubilizers are encapsulated, then coated with a heparin coating, then with a protective coating, then with an enteric coating.

The sodium taurocholate, Arlacel 186, safflower oil, Cremophor RH40, and propylene glycol are blended to form a liquid mixture, which is filled into capsules. A heparin sodium coating is then spray coated (200 mg/capsule) using an aqueous heparin sodium solution and a conventional pan coater. A protective coating of HPMC 603:PEG 6000:talc 4:1:4 ratio is then applied to a coating weight of ~70 mg/capsule. Finally, an enteric coating is applied with a solution of methacrylic acid/methacrylate copolymer aqueous dispersion (Eudragit L30- D55) with triethyl citrate (20%w/w copolymer) as plasticizer. Final enteric coating weight is about 90 mg.

EXAMPLE 18

A pharmaceutical dosage form is prepared containing the composition of EXAMPLE 12. In this dosage form the composition is granulated and compressed into tablets, which are then coated with a protective coating, then an enteric coating.

LMW heparin, ursodeoxycholic acid, and Gelucire 40/14 are mixed with corn starch (50% w/w with respect to the composition) and wet granulated with a solution of polyvinylpyrrolidone (Kollidon K30) such that the K30 dry polymer ratio is 5% w/w with respect to the composition. Finally, the granulation is mixed with magnesium stearate (2% w/w with respect the composition) and compressed into tablets.

A protective coating layer of polyvinylpyrrolidone-vinyl acetate copolymer and HPMC (Kollidon VA64:HPMC 603 1:5 ratio) is applied to the coated particles at 8% coating weight using a conventional coating pan. Finally, an enteric coating is applied at 10% coating weight using the method of Example 16.

EXAMPLE 19

A pharmaceutical dosage form is prepared containing the composition of EXAMPLE 13. In this dosage form, LMW heparin is mixed with lactose and spray dried. The spray dried particles are then coated with the surfactant mixture, then a bile acid coating, then with a protective coating, and finally with an enteric coating.

The LMW heparin and lactose (0.065:0.935 weight ratio) are dissolved in water, then spray dried and milled to 30/35 mesh. Maisine 35-1, PEG-40 monostearate, and PEG-1 50 monostearate are dissolved in isopropanol:methylene chloride 1:1 along with magnesium stearate (0.2% w/w with respect to surfactant mixture) and coated on the LMW heparin/lactose particles using a conventional coating pan to a coating weight of 30%. The bile acid coating is then applied to a coating weight of 6.8% using an ethanolic solution of chenodeoxycholic acid. A protective coating is then applied using polyvinylpyrrolidone (Kollidon K30, 5% in isopropanol) to a coating weight of ~8%. A final enteric coating (coating weight 10%) is applied using a solution of cellulose acetate phthalate in isopropanol with triacetin (20%wlw copolymer) as plasticizer.

EXAMPLE 20

A pharmaceutical dosage form is prepared containing the composition of EXAMPLE 11. In this dosage form the bile salt/surfactant components are coated on a bead substrate, which is then coated with a LWM heparin coating, then with a protective coating, then with an enteric coating.

The sodium taurocholate, glycerol monolaurate, Cremophor RH40, and PEG-1 50 monostearate are dissolved in isopropanol:methylene chloride 1:1 and spray coated on sugar beads (nonpareil seed; 30/35 mesh) using a fluidized bed coater to a coating weight of 30%. A LMW heparin coat is then applied using an aqueous solution to a coating weight of 5.1%. A protective coating is then applied using polyvinylpyrrolidone (Kollidon K30, 5% in isopropanol) to a coating weight of ~8%. A final enteric coating (10% coating weight) is applied with a using methacrylic acid/ methacrylate copolymer aqueous dispersion (Eudragit L30-D55) with triethyl citrate (20%w/w copolymer) as plasticizer.

EXAMPLE 21

A pharmaceutical dosage form is prepared containing the composition of EXAMPLE 14. In this dosage form the composition is mixed with polyvinylpyrrolidone and lactose and spray-dried into particles. The resulting particles are encapsulated in a gelatin capsule, which is then enteric coated.

Sodium ursodeoxycholate, LMW heparin, and Gelucire 50/13 are dissolved in water along with polyvinylpyrrolidone (Kollidon K30) and lactose at a ratio of 0.5:0.25:0.25 Composition:K30:Lactose. The solution is spray dried and milled to <30 MESH. The spray-dried powder is filled into gelatin capsules and the capsules are enteric coated using the technique described in Example 15.

EXAMPLE 22

A pharmaceutical dosage form is prepared containing the composition of EXAMPLE 14. In this dosage form the composition is spray dried into particles, which are then coated with an enteric coating, then a protective coating.

LMW heparin, sodium ursodeoxycholate, and Gelucire 50/13 are mixed are dissolved in water along with polyvinylpyrrolidone (Kollidon K30) and lactose at a ratio of 0.5:0.25:0.25 Composition:K30:Lactose. The solution is spray dried and milled to <30 MESH.

An enteric coating is applied with a solution of methacrylic acid/methacrylate copolymer aqueous dispersion (Eudragit L30- D55) with triethyl citrate (20%w/w copolymer) as plasticizer. A fmal protective coating is then applied using polyvinylpyrrolidone (Kollidon K30, 5% in isopropanol) in a fluidized bed coater to a coating weight of ~8%.

Absorption of Low Molecular Weight Heparin:

Absorption of low molecular weight heparin (LMW heparin) was evaluated using an in situ rat gut infusion model. The in situ oral absorption experiments were conducted by administering the composition into the duodenum of adult (300–400 g) male Sprague-Dawley rats through infusion. The rats were fasted from food for at least 8 hours prior to the experiments. Water was supplied ad libidum up until the time of surgery. Throughout the experiment, rats were anesthetized with 0.5–2% v/v halothane in oxygen from a halothane vaporizer (Vapomatic; A. M. Bickford Inc., N.Y.). Body temperature was maintained at 37° C. using a heating pad.

The compositions were dosed using a Teflon® cannula inserted into the duodenum 1 cm from the pylorus. The compositions were administered along with sufficient quantities of pH 7.4 isotonic buffer to achieve controlled dilution levels in the intestinal lumen. The quantity dosed and the volume of buffer infused were adjusted based on the animal body weight to achieve a fixed dilution in the buffer and to achieve a controlled LMW heparin dose/kg rat weight. The infusion rate was controlled with an isocratic syringe punp set to deliver the required volume within 60 minutes (typical flow rate=0.1 ml/min).

Blood samples were withdrawn at predetermined times by heart puncture with 29 gauge insulin syringes. The blood was immediately mixed with 3.8% (w/w) sodium citrate at a 1:9 citrate:blood ratio to prevent coagulation. Citrated blood was then centrifuged and the plasma separated for subsequent analysis using a heparin enzymatic assay.

In the heparin assay, citrated plasma samples were assayed using an enzymatic assay for heparin activity against coagulation factor Xa (Heparin Colorimetric Endpoint Assay Kit; Sigma Diagnostics; St. Louis, Mo.). This assay is designed to measure anti-Xa activity of both unfractionated and low-molecular weight heparin and was conducted as follows. Citrated plasma was equilibrated with excess antithrombin-III and Factor Xa, which form an inactive ternary complex with heparin. A chromogenic Xa specific substrate was then added and reacted for exactly 5 minutes before quenching with glacial acetic acid. The absorbance of the reacted Xa-substrate at 405 nm, measured with a UV/Vis spectrophotometer, is directly proportional to the residual Factor Xa and inversely proportional to the heparin activity in the plasma sample. Absorbance data were calibrated with solutions of known LMW heparin concentration prepared in plasma from each individual rat. When necessary, plasma samples were diluted with isotonic saline in order to obtain heparin concentrations within the linear range of the enzymatic assay (approximately 0.1–0.8 IU/ml).

EXAMPLE 23

We have found that the delayed-release dosage forms according to the present invention are advantageous in one aspect because they avoid the reduction in efficacy associated with excessive dilution of an absorption enhancing composition in gastric fluid. The test composition was diluted in two different concentrations to simulate the effect of a delayed release dosage form on the performance of the composition according to the present invention using the intraduodenal infusion rat model described above. An infusate made of the 10× dilution of the composition was used to simulate a delayed release dosage form releasing the absorption enhancing composition in the duodenum, and another infusate made of the 200× dilution of the composition was used to mimic a non-delayed release dosage form (e.g. a drink or a non-enteric coated dosage form taken with water) from which the composition is expected to be diluted in a large volume of gastric fluid in the stomach. In this example, the composition included LMW heparin, a bile salt (sodium chenodeoxycholate; Calbiochem, La Jolla Calif.), a non-ionic hydrophilic surfactant (PEG(40)-hydrogenated castor oil ester; Cremophor® RH40, BASF, Mount Olive N.J.), a hydrophobic surfactant (glycerol monooleate; Arlacel® 186, ICI Surfactants, Wilmington Del.), and a solubilizer (propylene glycol; Aldrich, Milwaukee, Wis.). The composition is summarized in Table 1 below as well as the control composition (containing LMW heparin only).

TABLE 1

| Composition Components and Amounts | | |
|---|---|---|
| Composition | Components | Weight (mg) |
| Composition A: Bile Salt + Hydrophilic Surfactant + Lipophilic Surfactant | Chenodeoxycholate Cremophor RH40 Arlacel 186 Propylene glycol LMW heparin | 130 340 320 210 10 |
| Control 1 | LMW heparin | 10 |

Table 2 summarizes the blood levels of LMW heparin resulting from composition A using different dilutions to simulate the effect of a delayed release dosage form on the performance of the composition. Composition A at 10× dilution (physiologically realistic dilution for an enteric coated dosage form releasing in the duodenum) resulted in a therapeutically relevant level of LMW heparin in plasma, while the composition dosed at 200× dilution (physiologically realistic dilution for a non-delayed release dosage form) resulted in no detectable level of LMW heparin in plasma. Control 1 with LMW heparin alone also resulted no detectable level of LMW heparin in plasma. The results demonstrate the importance of the delayed release dosage forms of the present invention to the performance of the absorption enhancing composition.

TABLE 2

Effect of dilution on LMW Heparin absorption from duodenal infusion at 1,500 Anti-Xa IU/kg LMW Heparin Dose

| Composition/ Dilution | LMW Heparin Plasma Concentration (Anti-Xa IU/ml) Mean ± SD, n = 2 unless otherwise specified | | | | |
|---|---|---|---|---|---|
| | t = 60 min | t = 90 min | t = 120 min | t = 180 min | $C_{max}$ |
| Composition A 10X dilution | 0.90 ± 0.07 | 1.6 ± 0.1 | 1.3 ± 0.1 | 1.25 ± 0.1 | 1.60 ± 0.1 |
| Composition A 200X dilution | ND[a] | ND[a] | ND[a] | ND[a] | — |
| Control 1 | ND[a] | ND[a] | ND[a] | ND[a] | — |

ND: Not detected; limit of detection = 0.05 IU anti-Xa/ml.
[a]n = 1 animal

Further illustrative examples of compositions producing significant LMW heparin plasma levels when tested in the delayed-release manner (10× dilution) are described below.

EXAMPLE 24

Additional compositions were tested under the dilution factor (10×) that would simulate the use of the delayed released dosage forms described in the present invention. According to the present invention, compositions B and D were prepared comprising of LMW heparin, a bile salt and a non-ionic hydrophilic surfactant (Cremophor® RH40). In addition, composition C and E were comprised of a bile salt, the hydrophilic surfactant, and a lipophilic surfactant (Arlacel® 186). Control compositions for composition B-E include LMW heparin alone (Control 2), LMW heparin with the non-ionic hydrophilic surfactant alone (Control 3) and LMW heparin with the lipophilic surfactant alone (Control 4). These compositions are summarized in Table 3 below.

TABLE 3

Composition Components and Amounts

| Composition | Components | Weight (mg) |
|---|---|---|
| Composition B: Bile Salt + Hydrophilic Surfactant | Ursodeoxycholate Cremophor RH40 Propylene glycol LMW heparin | 130 340 210 10 |
| Composition C: Bile Salt + Hydrophilic Surfactant + Lipophilic Surfactant | Ursodeoxycholate Cremophor RH40 Arlacel 186 Propylene glycol LMW heparin | 130 340 320 210 10 |
| Composition D: Bile Salt + Hydrophilic Surfactant | Chenodeoxycholate Cremophor RH40 LMW heparin | 130 340 10 |
| Composition E: Bile Salt + Hydrophilic Surfactant + Lipophilic Surfactant | Chenodeoxycholate Cremophor RH40 Arlacel 186 LMW heparin | 130 340 320 10 |
| Control 2 | LMW heparin | 60 |
| Control 3: Hydrophilic Surfactant | Cremophor RH40 LMW heparin | 340 60 |
| Control 4: Lipophilic Surfactant | Arlacel 186 LMW heparin | 300 60 |

In situ absorption experiments were conducted to measure LMW haprin plasma concentrations after intraduodenal administration of these compositions. The compositions were administered along with sufficient quantities of isotonic buffer to achieve a 10× dilution in the duodenum. Doses were adjusted based on rat weight to obtain a dose of 16.3 mg LMW heparin/kg (1,500 IU anti-Xa/kg) for Compositions B, C, D and E. Controls 2, 3 and 4 were administered at a higher dose (100 mg/kg; 9,200 IU 10 anti-Xa/kg) since the results in EXAMPLE 23 had shown that a higher dosing would be needed to produce detectable LMW heparin plasma levels with the controls. The pH of the aqueous dispersions was confirmed to be 7.6±0.2. The results of these in situ absorption experiments are shown in Table 4.

TABLE 4

In situ absorption of LMW heparin from duodenal infusion

| Composition | LMW Heparin Plasma Concentration (Anti-Xa IU/ml) Mean ± SD, n = 2 unless otherwise specified | | | | | $C_{max}$ Ratio to Control 2 (dose-normalized) |
|---|---|---|---|---|---|---|
| | t = 60 min | t = 90 min | t = 120 min | t = 180 min | $C_{max}$ | |
| Composition B: Bile Salt + Hydrophilic Surfactant | 0.42 ± 0.14 | 0.54 ± 0.41 | 0.60 ± 0.30 | 0.79 ± 0.16 | 0.79 ± 0.16 | 23 |
| Composition C: Bile Salt + Hydrophilic + Lipophilic Surfactant | 0.31 ± 0.22 | 0.62 ± 0.06 | 0.74 ± 0.17 | 0.89 ± 0.04 | 0.89 ± 0.04 | 26 |
| Composition D: Bile Salt + Hydrophilic Surfactant | 0.96 ± 0.39 | 0.8 ± 0.1 | 0.7 ± 0.1 | 0.5 ± 0.2 | 0.99 ± 0.4 | 29 |
| Composition E Bile Salt + Hydrophilic + Lipophilic Surfactant | 0.90 ± 0.07 | 1.6 ± 0.1 | 1.3 ± 0.1 | 1.25 ± 0.1 | 1.60 ± 0.1 | 47 |
| Control 2 | 0.05 ± 0.07[b] | 0.20 ± 0.02[b] | 0.19 ± 0.08 | 0.25[a] | 0.21 ± 0.04 | 1 |
| Control 3: Hydrophilic Surfactant | 0.10[a] | ND[a] | * | * | 0.10 | 0.5 |
| Control 4: Lipophilic Surfactant | 0.21[a] | 0.27[a] | * | * | 0.27 | 1.3 |

ND: Not detected, limit of detection = 0.05 IU anti-Xa/ml.
*: These experiments were terminated at 90 minutes.
[a] n = 1 animal
[b] n = 3 animals Compositions B, C, D and E were compared with the data for the Controls at the higher dosing (Controls 2–4) on a dose-normalized basis, since Control 1 (EXAMPLE 23) at a 1,500 Anti-Xa IU/kg dose did not produce detectable LMW heparin plasma levels in this model. With a delayed release dosage form, simulated by 10× dilution of the composition, the present invention containing a bile salt along with a hydrophilic or a lipophilic surfactant (Compositions B-E) resulted in therapeutically relevant levels of LMW heparin in plasma which were more than 20-fold higher than those from the LMW heparin only control on a dose-normalized basis.

EXAMPLE 25

We have also surprisingly found that the compositions of the present invention have enjoyed excellent compatibility with soft gelatin capsules. Briefly, a composition was prepared comprising sodium chenodeoxycholate/Arlacel® 186/Cremophor® RH40/propylene glycol in the respective proportions 130/320/340/210 by weight. This composition was filled into a 3ml syringe after gentle warming. It was then injected through an 18G 1&½ needle into air-filled soft gel capsules (Size 00, RP Scherer) from the elongated tip of the capsule. The injection site was heat-melted to seal the capsule. Each capsule was contained in a closed vial and stored at room temperature for observation. No leakage or brittleness was observed for any of the capsules over an 18 months test period.

We claim:

1. A delayed release pharmaceutical dosage form for oral adminisitraion of low moleclar weight heparin comprising a semi-solid, substantially nonaqueous composition of:
   (a) a therapeutically effective amount of low molecular weight heparin;
   (b) a bile salt or a bile acid that is suspended in the composition (i) in amorphous form, (ii) in milled, micronized, or nanosized form, or both (i) and (ii);
   (c) at least one hydrophilic surfactant and at least one lipoplilic surfactant; and
   (d) a means for delaying release of the composition from the dosage form following oral administration, wherein the bile salt or bile acid and the surfactants are selected such that upon mixing the composition with an aqueous mediuim at 100× dilution, an optically clear aqucous dispersion is formed having an absorbance of less than about 0.3 at 400 nm.

2. The dosage form of claim 1, comprising a capsule containing the composition.

3. The dosage form of claim 2, wherein the capsule is a starch capsule, a cellulosic capsule, a hard gelatin capsule or a soft gelatin capsule.

4. The dosage form of claim 1, comprising a tablet or caplet.

5. The dosage form of claim 1, comprising a plurality of particles, granules, beads, pellets or mixtures thereof.

6. The dosage form of any one of claims 1 through 5, wherein the means for delaying release comprises an enteric coating on the dosage form.

7. The dosage form of claim 1, wherein the low molecular weight heparin is present as a coating.

8. The dosage form of claim 1, wherein the bile salt or bile acid is present as a coating.

9. The dosage form of claim 8, wherein the means for delaying release comprises an enteric coating on the low molecular weight heparin coating.

10. The dosage form of claim 8, wherein the means for delaying release comprises an enteric coating on the bile salt or bile acid coating.

11. The dosage form of claim 2, wherein the composition is comprised of particles, granules, beads, pellets, or mixtures thereof.

12. The dosage form of claim 11, wherein the means for delaying release comprises an enteric coating on the particles, granules, beads, pellets, or mixtures thereof.

13. The dosage form of claim 11, wherein the particles, granules, beads, pellets, or mixtures thereof are coated with a coating comprised of low molecular weight heparin.

14. The dosage form of claim 11, wherein the particles, granules, beads, pellets, powder or mixtures thereof are coated with a coating comprised of a bile salt or bile acid.

15. The dosage form of claim 13, wherein the means for delaying release comprises an enteric coating on the low molecular weight heparin coating.

16. The dosage form of claim 14, wherein the means for delaying release comprises an enteric coating on the bile salt or bile acid coating.

17. The dosage form of claim 1, further including at least one protective coating.

18. The dosage form of claim 1, wherein the at least one hydrophilic surfactant is an ionic surfactant.

19. The dosage form of claim 1, wherein the at least one hydrophilic surfactant is a non-ionic surfactant having an HLB value of or greater than about 10.

20. The dosage form of claim 1, wherein the at least one lipophilic surfactant is a non-ionic surfactant having an HLB value of or less than about 10.

21. The dosage form of claim 1, wherein the at least one lipophilic surfactant is an unionized ionizable surfactant.

22. The dosage form of claim 1, wherein the at least one hydrophilic surfactant is a non-ionic surfactant having an HLB value of or greater than about 10 and the at least one lipophilic surfactant is a non-ionic surfactant having an HLB value of or less than about 10.

23. The dosage form of claim 1, wherein the low molecular weight heparin has a molecular weight in the range of approximately 1000 to 10,000 D.

24. The dosage form of claim 1, wherein the bile salt or bile acid is selected from cholic acid, ursodeoxycholic acid, chenodeoxycholic acid, deoxycholic acid, taurocholic acid, taurodeoxycholic acid, taurochenodeoxycholic acid, tauroursodeoxycholic acid, glycocholic acid, glycochenodeoxycholic acid, glycoursodeoxycholic acid, glycodeoxycholic acid, lithocholic acid, salts of any of the foregoing, and combinations thereof.

25. The dosage form of claim 24, wherein the bile salt or bile acid is ursodeoxycholic acid or a salt thereof.

26. The dosage form of claim 24, wherein the bile salt or bile acid is chenodeoxycholic acid or a salt thereof.

27. A delayed release dosage form for oral administration, comprised of a capsule coated with a biocrodible, gradually hydrolyzable, and/or gradually water-soluble enteric coating, and containing a liquid or semi-solid composition of low molecular weight heparin, a bile salt or acid that is suspended in the composition (i) in amoiorhous form, (ii) in milled, micronized, or nanosized form, or both (i) and (ii), and at least one surfactant selected from hydrophilic surfactants, lipoplhilic surfactants, and mixtures thereof, wherein any water present in the composition is insufficient to form a continuous aqueous phase, and further wherein the bile salt or bile acid and the at least one surfactant are selected such that upon mixing the composition with an aqueous medium at 100× dilution, an optically clear aqueous dispersion is formed having an absorbance of less than about 0.3 at 400 nm.

28. The dosage form of claim 27, wherein the enteric coating is comprised of a cellulosic polymer.

29. The dosage form of claim 28, wherein the cellulosic polymer is selected from hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate, carboxymethylcellulose sodium, and mixtures thereof.

30. The dosage form of claim 27, wherein the enteric coating is comprised of an acrylic acid polymer.

31. The dosage form of claim 30, wherein the acrylic acid polymer is a copolymer of acrylic acid, methacrylic acid, methyl acrylate, ammonio methylacrylate, ethyl acrylate, methyl methacrylate and/or ethyl methacrylate.

32. The dosage form of claim 27, wherein the enteric coating is comprised of a vinyl polymer selected from polyvinyl pyrrolidone, polyvinyl acetate, polyvinylacetate phthalate, vinylacetate crotonic acid copolymer, and ethylene-vinyl acetate copolymers.

33. A pharmaceutical composition comprised of a liquid or semi-solid composition of a therapeutically effective amount of low molecular weight heparin, a bile salt or bile acid that is suspended in the composition (i) in amorphous form, (ii) in milled, micronized, or nanosized form, or both (i) and (ii), and at least one surfactant selected from hydrophilic surfactants, lipophilic surfactants, and mixtures thereof, wherein the composition is substantially free of glycerol triesters of $C_6$ to about $C_{25}$ fatty acids.

34. The composition of claim 33, further including a solubilizer.

35. The composition of claim 34, wherein the solubilizer is selected from alcohols, polyols, ethers, amides, esters, and mixtures thereof.

36. The composition of claim 35, wherein the solubilizer is selected from water, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol, glycofurol, diethylene glycol monoethyl ether, propylene glycol, sorbitol, glycerol, ethanol, dimethyl isosorbide, and mixtures thereof.

37. The composition of claim 33, wherein the low molecular weight heparin is partially suspended in the composition.

38. The composition of claim 33, wherein the bile salt or bile acid is at least partially solubilized in the composition.

39. The composition of claim 33, wherein the bile salt or bile acid is in milled, micronized, or nanosized form.

40. The composition of claim 33, wherein the bile salt or bile acid is selected from cholic acid, ursodeoxycholic acid, chenodeoxycholic acid, deoxycholic acid, taurocholic acid, taurodeoxycholic acid, taurochenodeoxycholic acid, tauroursodeoxycholic acid, glycocholic acid, glycochenodeoxycholic acid, glycoursodeoxycholic acid, glycodeoxycholic acid, lithocholic acid, salts of any of the foregoing, and combinations thereof.

41. The composition of claim 40, wherein the bile salt or bile acid is ursodeoxycholic acid or a salt thereof.

42. The composition of claim 40, wherein the bile salt or bile acid is chenodeoxycholic acid or a salt thereof.

43. The composition of claim 33, wherein any water present in the composition is insufficient to form a continuous aqueous phase.

44. The composition of claim 33, wherein the bile salt or bile acid and the at least one surfactant are selected such that upon mixing with an aqueous medium at 100× dilution, an optically clear aqueous dispersion is formed having an absorbance of less than about 0.3 at 400 nm.

45. A drug delivery system for oral administration of a polysaccharide drug, comprising: a first dosage form containing a therapeutically effective amount of the polysaccharide drug; and a second dosage form containing a bile salt or bile acid, in combination with at least one surfactant selected from hydrophilic surfactants, lipophilic surfactants, and mixtures thereof, wherein at least one of the dosage forms is a delayed release dosage form.

46. The drug delivery system of claim 45, wherein the second dosage form and optionally the first dosage form are coated with an enteric coating.

47. The drug delivery system of claim 45, wherein the polysaccharide drug is selected from glucosamine, glycosaminoglycans, dextran, xylan, pentasaccharide, polygalacturonic acid, polymannuronic acid, chitin, pharmaceutically acceptable salts, esters or other derivatives thereof, and combinations of any of the foregoing.

48. The drug delivery system of claim 47, wherein the polysaccharide drug is a glycosaminoglycan.

49. The drug delivery system of claim 48, wherein the glycosaminoglycan is selected from heparin, heparan, chondroitin, dermatan, hyaluronic acid and pharmaceutically acceptable salts thereof.

50. The drug delivery system of claim 48, wherein the glycosaminoglycan is selected from heparin, low molecular weight heparin, heparin sodium, heparan sulfate, and pharmaceutically acceptable salts of any of the foregoing formed with metallic cations or organic bases.

51. The drug delivery system of claim 50, wherein the polysaccharide drug is low molecular weight heparin.

52. The drug delivery system of claim 50, wherein the polysaccharide drug is heparin sodium.

53. The drug delivery system of claim 50, wherein the polysaccharide drug is heparan.

54. The drug delivery system of claim 50, wherein the polysaccharide drug is heparan sulfate.

55. In a method for administering low molecular weight heparin to a patient, the improvement comprising orally administering the low molecular weight heparin to the patient in the delayed release pharmaceutical dosage form of claim 1.

56. A method for administering a polysaccharide drug to a patient, comprising orally administering to the patient: a first dosage form containing a therapeutically effective amount of the polysaccharide drug; and a second dosage form containing a bile salt or bile acid, in combination with at least one surfactant selected from hydrophilic surfactants, lipophilic surfactants, and mixtures thereof, wherein at least one of the dosage forms is a delayed release dosage form.

57. The method of claim 56, wherein the two dosage forms are administered simultaneously.

58. The method of claim 56, wherein the first dosage form is administered before the second dosage form is administered.

59. The method of claim 56, wherein the first dosage form is administered after the second dosage form is administered.

60. A pharmaceutical dosage form for oral administration, comprising: an osmotically activated device coated with a bioerodible, gradually hydrolyzable, and/or gradually water-soluble enteric coating, and housing a composition containing a therapeutically effective amount of a hydrophilic drug, a bile salt or bile acid that is in amorphous form, is at least partially solubilized in the composition, and/or has been milled, micronized, or nanosized, and at least one surfactant selected from hydrophilic surfactants, lipophilic surfactants, and mixtures thereof, wherein the bile salt or bile acid and the at least one surfactant are selected such that upon mixing the composition with an aqueous medium at 100× dilution, an optically clear aqueous dispersion is formed having an absorbance of less than about 0.3 at 400 nm.

61. A delayed release pharmaceutical dosage form for oral administration of a polysaecharide drug, comprising a semisolid, substantially nonaqueous composition of:
   (a) a therapeutically effective amount of a polysaecharide drug;
   (b) a bile salt or bile acid that is suspended in the composition (i) in amorphous form, (ii) in milled, micronized, or nanosized form, or both (i) and (ii);
   (c) at least one hydrophilic surfactant and at least one lipophilic surfactant; and
   (d) a means for delaying release of the composition of the dosage form following oral administration, wherein the bile salt or bile acid and the surfactants are selected such that upon mixing the composition with an aqueous medium at 100× dilution, an optically clear aqueous dispersion is formed having an absorbance of less than about 0.3 at 400 nm.

62. The dosage form of claim 61, wherein the polysaccharide drug is selected from glucosamine, glycosaminoglycans, dextran, xylan, pentasaccharide, polygalacturonic acid, polymannuronic acid, chitin, pharmaceutically acceptable salts, esters or other derivatives thereof, and combinations of any of the foregoing.

63. The dosage form of claim 62, wherein the polysaccharide drug is a glycosaminoglycan.

64. The dosage form of claim 63, wherein the glycosaminoglycan is selected from heparin, heparan, chondroitin, dermatan, hyaluronic acid and pharmaceutically acceptable salts thereof.

65. The dosage form of claim 63, wherein the glycosaminoglycan is selected from heparin, low molecular weight heparin, heparin sodium, heparan sulfate, and pharmaceutically acceptable salts of any of the foregoing formed with metallic cations or organic bases.

66. The dosage form of claim 65, wherein the polysaccharide drug is low molecular weight heparin.

67. The dosage form of claim 65, wherein the polysaccharide drug is heparin sodium.

68. The dosage form of claim 65, wherein the polysaccharide drug is heparan.

69. The dosage form of claim 65, wherein the polysaccharide drug is heparan sulfate.

70. A delayed release pharmaceutical dosage form comprising: (a) a therapeutically effective amount of low molecular weight heparin, and (b) at least one hydrophilic surfactant and at least one lipophilic surfactant, wherein the dosage form is coated with (c) a coating comprised of a bile salt or bile acid that is in amorphous form, and/or has been milled, micronized, or nanosized, and (d) an outermost layer of an enteric coating thereon.

71. A delayed release pharmaceutical dosage form comprising: (a) a bile salt or acid that is in amorphous form, and/or has been milled, micronized, or nanosized, and (b) at least one hydrophilic surfactant and at least one lipophilic surfactant, wherein the dosage form is coated with (c) a coating comprised of low molecular weight heparin, and (d) an outermost layer of an enteric coating thereon.

72. The dosage form of claim 1, wherein the bile salt or acid is in amorphous form.

73. The dosage form of claim 72, wherein the amorphous bile salt or acid is in milled, micronized, or nanosized form.

74. The dosage form of claim 27, wherein the bile salt or acid is in amorphous form.

75. The dosage form of claim 74, wherein the amorphous bile salt or acid is in milled, micronized, or nanosized form.

76. The composition of claim 33, wherein the bile salt or acid is in amorphous form.

77. The composition of claim 76, wherein the amorphous bile salt or acid is in milled, micronized, or nanosized form.

78. The dosage form of claim 60, wherein the bile salt or acid is in amorphous form.

79. The dosage form of claim 78, wherein the amorphous bile salt or acid is in milled, micronized, or nanosized form.

80. The dosage form of claim 61, wherein the bile salt or acid is in amorphous form.

81. The dosage form of claim 80, wherein the amorphous bile salt or acid is in milled, micronized, or nanosized form.

82. The dosage form of claim 70, wherein the bile salt or acid is in amorphous form.

83. The dosage form of claim 82, wherein the amorphous bile salt or acid is in milled, micronized, or nanosized form.

84. The dosage form of claim 71, wherein the bile salt or acid is in amorphous form.

85. The dosage form of claim 84, wherein the amorphous bile salt or acid is in milled, micronized, or nanosized form.

86. In a method for administering low molecular weight heparin to a patient, the improvement comprising orally administering the low molecular weight heparin to the patient in the delayed release pharmaceutical dosage form of claim 27.

87. In a method for administering low molecular weight heparin to a patient, the improvement comprising orally administering the low molecular weight heparin to the patient in the composition of claim 33.

88. In a method for administering low molecular weight heparin to a patient, the improvement comprising orally administering the low molecular weight heparin to the patient in the delayed release pharmaceutical dosage form of claim 70.

89. In a method for administering low molecular weight heparin to a patient, the improvement comprising orally administering the low molecular weight heparin to the patient in the delayed release pharmaceutical dosage form of claim 71.

90. A delayed release pharmaceutical dosage form for oral administration of low molecular weight heparin comprising a solid composition of:
   (a) a therapeutically effective amount of low molecular weight heparin;
   (b) a bile salt or a bile acid in amorphous form and/or milled, micronized, or nanosized form;
   (c) at least one surfactant selected from hydrophilic surfactants, lipophilic surfactants, and mixtures thereof; and
   (d) a means for delaying release of the composition from the dosage form following oral administration.

91. The dosage form of claim 1, wherein the composition further includes an additional quantity of the bile salt or acid that is in solubilized form, such that the bile salt or acid is partially solubilized and partially suspended in the composition.

92. The dosage form of claim 27, wherein the composition further includes an additional quantity of the bile salt or acid in solubilized form, such that the bile salt or acid is partially soltubilized and partially suspended in the composition.

93. The composition of claim 33, further including an additional quantity of the bile salt or acid in solubilized form, such that the bile salt or acid is partially solubilized and partially suspended in the composition.

94. The dosage form of claim 61, wherein the composition further includes an additional quantity of the bile salt or acid in solubilized form, such that the bile salt or acid is partially solubilized and partially suspended in the composition.

* * * * *